United States Patent
Tyrrell et al.

(10) Patent No.: US 9,969,979 B2
(45) Date of Patent: May 15, 2018

(54) METHODS FOR PRODUCING CELLS HAVING A PHENOTYPE OF A PRIMARY HUMAN HEPATOCYTES AND COMPOSITIONS

(71) Applicant: The Governors of the University of Alberta, Edmonton (CA)

(72) Inventors: D. Lorne Tyrrell, Edmonton (CA); Hendrikje Geesje Steenbergen, Edmonton (CA); Michael A. Joyce, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 155 days.

(21) Appl. No.: 14/423,991

(22) PCT Filed: Aug. 30, 2013

(86) PCT No.: PCT/IB2013/002501
§ 371 (c)(1),
(2) Date: Feb. 25, 2015

(87) PCT Pub. No.: WO2014/033546
PCT Pub. Date: Mar. 6, 2014

(65) Prior Publication Data
US 2015/0184124 A1     Jul. 2, 2015

Related U.S. Application Data

(60) Provisional application No. 61/761,588, filed on Feb. 6, 2013, provisional application No. 61/696,059, filed on Aug. 31, 2012.

(51) Int. Cl.
*C12N 5/071* (2010.01)
*G01N 33/50* (2006.01)
*C12N 7/00* (2006.01)

(52) U.S. Cl.
CPC ............... *C12N 5/067* (2013.01); *C12N 7/00* (2013.01); *G01N 33/5014* (2013.01); *G01N 33/5026* (2013.01); *G01N 33/5067* (2013.01); *C12N 2500/84* (2013.01); *C12N 2503/02* (2013.01); *C12N 2506/30* (2013.01); *C12N 2730/10152* (2013.01); *C12N 2770/24252* (2013.01)

(58) Field of Classification Search
CPC ...................................................... C12N 5/067
USPC ............................................................. 506/9
See application file for complete search history.

(56) References Cited

U.S. PATENT DOCUMENTS

| | | | |
|---|---|---|---|
| 5,798,250 A | 8/1998 | Zeytinoglu | |
| 6,096,541 A | 8/2000 | Houghton et al. | |
| 6,146,873 A | 11/2000 | Kistner et al. | |
| 6,387,662 B1 | 5/2002 | Liang et al. | |
| 6,458,585 B1 | 10/2002 | Vachula et al. | |
| 7,351,584 B2 | 4/2008 | Silber et al. | |
| 7,455,969 B2 | 11/2008 | Rice, III et al. | |
| 7,456,018 B2 | 11/2008 | Gripon et al. | |
| 7,575,859 B2 | 8/2009 | Silber et al. | |
| 7,575,911 B2 | 8/2009 | Silber et al. | |
| 7,759,087 B1 | 7/2010 | Tang | |
| 7,939,248 B2 | 5/2011 | Silber et al. | |
| 2002/0015999 A1 | 2/2002 | Biddle et al. | |
| 2003/0162167 A1 | 8/2003 | Houghton et al. | |
| 2004/0229336 A1 | 11/2004 | Andre et al. | |
| 2005/0084965 A1 | 4/2005 | Silber et al. | |
| 2007/0292840 A1 | 12/2007 | Lemon et al. | |
| 2008/0274535 A1 | 11/2008 | Silber et al. | |
| 2008/0286752 A1 | 11/2008 | Singh | |
| 2008/0286759 A1 | 11/2008 | Brown et al. | |
| 2010/0035298 A1 | 2/2010 | Brown et al. | |
| 2010/0068698 A1 | 3/2010 | McCown et al. | |
| 2011/0027891 A1 | 2/2011 | Jorquera Nieto et al. | |

FOREIGN PATENT DOCUMENTS

| | | |
|---|---|---|
| EP | 1213030 | 6/2002 |
| WO | WO 1996/024662 | 8/1996 |
| WO | WO 1998/006823 | 2/1998 |
| WO | WO 1998/006826 | 2/1998 |
| WO | 1999/67362 | 12/1999 |
| WO | WO 2002/077206 | 10/2002 |
| WO | WO 2003/011209 | 2/2003 |
| WO | WO 2007/046962 | 4/2007 |
| WO | WO 2009/025759 | 2/2009 |
| WO | WO 2010/028999 | 3/2010 |
| WO | 2010/123357 | 10/2010 |

OTHER PUBLICATIONS

Nakabayashi et al. (Cancer Research, Sep. 1982, 42, pp. 3858-3863).*
Cánovas et al. (Altex 29, Apr. 2012, pp. 426-428).*
Ryan (Corning, Subculturing Monolayer Cell Cultures Protocol, Aug. 2004, pp. 1-5).*
HepG2: cell culture and transfection protocol (http://www.hepg2.com, 2017) (Year: 2017).*
Akazawa et al. (2011) "Production and characterization of HCV particles from serum-free culture," *Vaccine*; 29:4821-4828.
Banaudha et al. (2010) "Primary hepatocyte culture supports hepatitis C virus replication: A model for infection-associated hepatocarcinogenesis," *Hepatology*; 51(6) :1922-1932.

(Continued)

*Primary Examiner* — Karla A Dines
(74) *Attorney, Agent, or Firm* — Shweta Chandra; Carol L. Francis; Bozicevic, Field & Francis LLP

(57) ABSTRACT

The present disclosure provides methods and compositions relating to in vitro cultures of human hepatocyte cell lines which exhibit a primary human hepatocyte phenotype. Such cell lines are susceptible to infection by a hepatotrophic virus, such as HCV or HBV, and support both viral replication and high levels of viral particle production. Such in vitro cultures find use in production and study of hepatotrophic virus, as well as methods of screening (e.g., for antiviral drugs, assessing drug metabolism), and study of primary human hepatocytes.

25 Claims, 20 Drawing Sheets

(56) References Cited

OTHER PUBLICATIONS

Bartosch et al. (2005) "An Interplay between Hypervariable Region 1 of the Hepatitis C Virus E2 Glycoprotein, the Scavenger Receptor BI, and High-Density Lipoprotein Promotes both Enhancement of Infection and Protection against Neutralizing Antibodies," *J. Virol.*; 79(13):8217-8229.
Blais et al. (2010) "Activity-based Protein Profiling Identifies a Host Enzyme, Carboxylesterase 1, Which Is Differentially Active during Hepatitis C Virus Replication," *J Biol Chem*; 285:25602-25612.
Blais et al. (2010) "Activity-Based Proteome Profiling of Hepatoma Cells during Hepatitis C Virus Replication Using Protease Substrate Probes," *J Proteome Res*; 9:912-923.
Brousseau et al. (1993) "Sequential ultracentrifugation micromethod for separation of serum lipoproteins and assays of lipids, apolipoproteins, and lipoprotein particles," *Clinical Chemistry*; 39(6):960-964.
Hino et al. (1999) "A long-term culture of human hepatocytes which show a high growth potential and express their differentiated phenotypes," *Biochem. Biophys. Res. Commun.*; 256:184-191.
Jennen et al. (2010) "Nontargeted Modification-Specific Metabolomics Study Based on Liquid Chromatography-High-Resolution Mass Spectrometry," *Drug Discovery Today*; 15:851-858.
Joyce et al. (2009) "HCV Induces Oxidative and ER Stress, and Sensitizes Infected Cells to Apoptosis in SCID/Alb-uPA Mice," *PLoS pathogens*; 5:e1000291.
Katsura et al. (2002) "Long-term culture of primary human hepatocytes with preservation of proliferative capacity and differentiated functions," *J. Surg. Res.*; 106:115-123.
Ladner et al. (1997) "Inducible Expression Of Human Hepatitis B Virus (Hbv) in Stably Transfected Hepatoblastoma Cells: A Novel System for Screening Potential Inhibitors Of Hbv Replication," *Natl. Center Biotech. Info.*; 41(8):1715-1720.
Lavillette et al. (2005) "Human Serum Facilitates Hepatitis C Virus Infection, and Neutralizing Responses Inversely Correlate with Viral Replication Kinetics at the Acute Phase of Hepatitis C Virus Infection," *J. Virol.*; 79(10):6023-6034.
Li et al. (2009) "A genome-wide genetic screen for host factors required for hepatitis C virus propagation," *Proc Natl Acad Sci USA*; 106(38):16410-16415.
Lindenback et al. (2005) "Complete Replication of Hepatitis C Virus in Cell Culture," *Science*; 309:623-626.
Ling et al. (2013) "Characterization of lipid and lipoprotein metabolism in primary human hepatocytes," *Biochim Biophys Acta*; 1831(2):387-397.
Marion et al. (2010) "The HepaRG cell line: biological properties and relevance as a tool for cell biology, drug metabolism, and virology studies," *Mol. Biol.*; 640:261-272.
McCown and Najera (2010) "Production of Infectious Hepatitis C Virus Particles in Cell Culture," *Patentdocs*; 1-40.
Meex et al. (2011) "Huh-7 or HepG2 cells: which is the better model for studying human apolipoprotein-B100 assembly and secretion?" *J Lipid Res*; 52(1):152-158.
Mercer et al. (2001) "Hepatitis C virus replication in mice with chimeric human livers," *Nat Med.*; 7(8):927-933.
Pfaffl (2001) "A new mathematical model for relative quantification in real-time RT-PCR," *Nucl. Acids Res.*; 29(9):2002-2007.
Ploss et al. (2010) "Persistent hepatitis C virus infection in microscale primary human hepatocyte cultures," *Proc. Natl. Acad. Sciences*; 107(7):3141-3145.
Podevin et al. (2010) "Production of infectious hepatitis C virus in primary cultures of human adult hepatocytes," *Gastroenterology*; 139:1355-1364.
Poyck et al. (2008) "Evaluation of a new immortalized human fetal liver cell line (cBAL111) for application in bioartificial liver," *J. Hepatol.*; 48(2):266-275.
Reiss et al. (2011) "Recruitment and Activation of a Lipid Kinase by Hepatitis C Virus NS5A Is Essential for Integrity of the Membranous Replication Compartment," *Cell Host Microbe*; 9:32-45.
Sainz et al. (2006) "Production of Infectious Hepatitis C Virus by Well-Differentiated, Growth-Arrested Human Hepatoma-Derived Cells," *J Viral*; 80:10253-10257.
Singaravelu et al. (2010) "Activity-based protein profiling of the hepatitis C virus replication in Huh-7 hepatoma cells using a non-directed active site probe," *Proteome Sci*; 8:5.
Steenbergen et al. (2010) "Lipoprotein profiles in SCID/uPA mice transplanted with human hepatocytes become human-like and correlate with HCV infection success," *Am J Physiol Gastrointest Liver Physiol*; 299: G844-G854.
Walters et al. (2006) "Application of functional genomics to the chimeric mouse model of HCV infection: optimization of microarray protocols and genomics analysis," *Virology Journal*; 3:37.
Walters et al. (2006) "Host-Specific Response to HCV Infection in the Chimeric SCID-beige/Alb-uPA Mouse Model: Role of the Innate Antiviral Immune Response," *PLoS pathogens*; 2:e59.
Yan et al. (2012) "Sodium taurocholate cotransporting polypeptide is a functional receptor for human hepatitis B and D virus," *eLife*; 1:e00049.
Yang et al. (2012) "A simple and sensitive method for lipoprotein and lipids profiles analysis of individual micro-liter scale serum samples," *Chem Phys Lipids*; 165(2):133-141.
Yi et al. (2006) "Production of infectious genotype 1a hepatitis C virus (Hutchinson strain) in cultured human hepatoma cells," *Proc. Natl. Acad. Sciences*; 103(7):2310-2315.
Zhong et al. (2005) "Robust hepatitis C virus infection in vitro," *PNAS*; 102(26):9294-9299.
Zirpoli et al. (2012) "Selective action of human sera differing in fatty acids and cholesterol content on in vitro gene expression," *J Cell Biochem.*; 113:815-823.
ATCC PTA-8561 (2012) "Cell Line: Huh7.5 p#30;2X10e6;Mar. 27, 2007 (PTA8561)" 1 pg.
ATCC Product Sheet (2015) "Hep G2 [HEPG2] (ATCC® HB8065™)" 3 pgs.
ATCC Product Sheet (2015) "C3A [HepG2/C3A, derivative of Hep G2 (ATCC HB8065)] (ATCC® CRL10741™)" 3 pgs.

\* cited by examiner

Huh7.5 cells grown in FBS containing medium

Huh7.5 cells maintained in HS containing medium for 21 days

Human primary hepatocytes grown on collagen coated dishes

METHODS FOR PRODUCING CELLS HAVING A PHENOTYPE OF A PRIMARY HUMAN HEPATOCYTES AND COMPOSITIONS

CROSS-REFERENCE TO RELATED APPLICATIONS

This application claims priority benefit of U.S. provisional application Ser. No. 61/696,059, filed Aug. 31, 2012 and U.S. provisional application Ser. No. 61/761,588, filed Feb. 6, 2013, each of which applications is incorporated herein by reference in its entirety.

INTRODUCTION

Hepatitis C virus (HCV) is small enveloped, positive-strand RNA virus of the family of Flaviviridae that causes acute and chronic hepatitis. It can cause cirrhosis, hepatocellular carcinoma and steatosis in affected individuals. The 9.6 kb genome of HCV consists of a single open reading frame, encoding an about 3,000 amino acid polyprotein that is cleaved co- and post-translationally. Several studies have reported human factors that support HCV infection (Li et al. (2009) Proc Natl Acad Sci USA 106: 16410-16415; Reiss et al. (2011) Cell Host Microbe 9: 32-45). A significant number of these factors play a role in vesicle organization, or membrane and lipid related genes. On the other hand, HCV proteins are also known to induce transcriptional changes in infected cells (Blais et al. (2010) J Proteome Res 9: 912-923; Blais et al. (2010) J Biol Chem 285: 25602-25612; Joyce et al. (2009) PLoS pathogens 5: e1000291; Singaravelu et al. (2010) Proteome Sci 8:5; Walters et al. (2006) Virology Journal 3:37; Walters et al. (2006) PLoS pathogens 2: e59), for example by the formation of the membranous web, modulation of innate immunity pathways and induction of lipid synthesis pathways.

Subgenomic, full-length replicon systems and JFH-1 infection models have yielded insight into HCV translation and RNA replication, entry and egress. Most of these models are based on HuH-7 or HuH-7 derived cells. The use of HuH-7 (or -derived) cells has many advantages for the in vitro study of HCV. They are readily available, are rapidly dividing and therefore enable large-scale experiments. However, these systems do not necessarily accurately represent the events that occur during a natural HCV infection in vivo, since hepatocytes are normally non-dividing and fully differentiated. Efforts have been taken to circumvent this, by growth arrest of cells by adding 1-2% dimethyl sulfoxide (DMSO, a polar aprotic solvent) to the cell culture medium (Sainz et al. (2006) J Virol 80: 10253-10257), resulting in the induction of expression of hepatocyte-specific genes.

Freshly isolated primary human hepatocytes are logically a more representative in vitro model to study HCV infectivity. However, the amount of virus produced in these cells is low (typically less than $10^3$ RNA copies/ml), and for long term experiments (more than a few days) these cells have to be co-cultured with other cell types (Banaudha et al (2010) Hepatology, 51: 1922-1932; Ploss et al. Proc. Natl. Acad. Sciences 2010 vol. 107 no. 7 3141-3145). Primary hepatocytes are thus not suitable for large scale virus production.

HCV viral titers have been achieved in HuH-7 or HuH-7-derived cells of approximately $10^6$ to $10^7$ RNA copies per ml (about 1 virus per cell). However, these viral titers are generally too low to provide for commercial scale production of viral particles. Additionally, infection in HuH7.5 cells has only been possible with an atypical HCV variant, JFH-1.

There is a need in the field for a culture system that can serve as an in vitro model of primary human hepatocytes.

SUMMARY

The present disclosure provides methods and compositions relating to in vitro cultures of human hepatocyte cell lines which exhibit a primary human hepatocyte phenotype. Such cell lines are susceptible to infection by a hepatotrophic virus, such as HCV or HBV, and support both viral replication and high levels of viral particle production. Such in vitro cultures find use in production and study of hepatotrophic virus, as well as methods of screening (e.g., for antiviral drugs, assessing drug metabolism), and study of primary human hepatocytes.

The present disclosure provides methods of producing a cell culture comprising cells having a primary human hepatocyte phenotype, which method comprises culturing a human hepatocellular carcinoma (hHCC) cell line in a culture medium comprising human serum for more than 11 days, wherein said culturing induces differentiation of the hHCC cell line into a cell having a primary human hepatocyte phenotype. In some embodiments, the culture medium comprises from about 1% to 20% human serum, optionally from about 2% to 10% human serum. In some embodiments, the hHCC cell line is a HuH-7 or HuH-7-derived cell line. In some embodiments, the culturing is conducting without subculturing after 10 days of culturing in the culture medium comprising human serum. The present disclosure further provides cell cultures comprising cells produced by such culturing methods.

The present disclosure provides cell cultures comprising cells having a phenotype of a human primary hepatocyte, wherein the cells are the differentiated progeny of an hHCC cell line; and a culture medium comprising human serum. In some embodiments, the cell culture has been continuously maintained for at least 7 days, at least 8 days, at least 10 days, at least 11 days, at least 12 days, at least 13 days, at least 14 days, at least 15 days, at least 16 days, at least 17, days at least 18 days, at least 19 days, at least 20 days, or at least 21 days, or more. In some embodiments, the culture medium comprises from about 1% to 20% human serum, optionally from about 2% to 10% human serum. In some embodiments, the hHCC cell line is a HuH-7 or HuH-7-derived cell line.

The present disclosure provides methods for assessing an effect of a candidate agent on a cell having a phenotype of a human primary hepatocyte comprising contacting a differentiated cell culture of the present disclosure with a candidate agent; and assaying for the presence of absence of an effect of the candidate agent on a phenotype of the cell having a phenotype of a human primary hepatocyte. In some embodiments, assaying is for an effect of the candidate agent on lipid metabolism by the cell having a phenotype of a primary human hepatocyte. In other embodiments, assaying is for an effect of the candidate agent on very low density lipoprotein (VLDL), low density lipoprotein (LDL), and/or high density lipoprotein (HDL) secretion by the cell having a phenotype of a primary human hepatocyte.

The present disclosure provides methods for assessing metabolism of an agent by a cell having a phenotype of a human primary hepatocyte comprising contacting a differentiated cell culture of the present disclosure with an agent; and assaying for the presence of absence of a metabolite of the agent and/or the agent. In some embodiments, the agent is a drug.

The present disclosure provides methods for assessing toxicity of an agent on a cell having a phenotype of a human primary hepatocyte comprising contacting a differentiated cell culture of the present disclosure with an agent; and assaying for the presence of absence of a change in a phenotype of the cell which is indicative of toxicity of the agent for the cell. In some embodiments, the phenotype assayed is an increase in transaminase in culture medium and/or assaying for a marker of cell death.

The present disclosure provides methods of producing viral particles comprising incubating a cell culture comprising a human hepatocellular carcinoma (hHCC) cell line in a culture medium comprising human serum for more than 11 days, wherein said incubating induces differentiation of the hHCC cell line into a cell having a primary human hepatocyte phenotype; introducing a genome of a hepatotrophic virus into at least one of the hHCC cell line or the cell having primary human hepatocyte phenotype; and maintaining the cell culture under conditions suitable for production of viral particles. In some embodiments, the viral genome is introduced by adding infectious viral particles to the culture medium. In some embodiments, the infectious viral particles are added at day 1 of said culturing. In some embodiments, the viral genome is introduced into the hHCC cell line prior to said incubating. In some embodiments of these methods, the method comprises isolating viral particles from the culture medium.

The present disclosure provides virally-infected cell cultures comprising cells produced by a method comprising incubating a cell culture comprising a human hepatocellular carcinoma (hHCC) cell line in a culture medium comprising human serum for more than 11 days, wherein said culturing induces differentiation of the hHCC cell line into a cell having a primary human hepatocyte phenotype; and introducing a genome of a hepatotrophic virus into at least one of the hHCC cell line or the cell having primary human hepatocyte phenotype.

The present disclosure provides methods for screening a candidate agent for antiviral activity comprising incubating a cell culture comprising a human hepatocellular carcinoma (hHCC) cell line in a culture medium comprising human serum for more than 11 days, wherein said incubating induces differentiation of the hHCC cell line into a cell having a primary human hepatocyte phenotype; introducing a genome of a hepatotrophic virus into at least one of the hHCC cell line or the cell having primary human hepatocyte phenotype; contacting the cell culture with a candidate antiviral agent; maintaining the cell culture under conditions suitable for viral replication; and detecting the presence or absence of an effect of the candidate agent upon viral replication; wherein a decrease in viral particle production in the presence of the candidate agent as compared to the absence of the candidate agent indicates the candidate agent have antiviral activity. In some embodiments, the viral genome is introduced by adding infectious viral particles to the culture medium. In some embodiments, the infectious viral particles are added at day 1 of said culturing. In some embodiments, the viral genome is introduced into the hHCC cell line prior to said incubating.

The present disclosure provides methods for screening a sample suspected of containing an antibody for antiviral activity comprising: incubating a cell culture comprising a human hepatocellular carcinoma (hHCC) cell line in a culture medium comprising human serum for more than 11 days, wherein said incubating induces differentiation of the hHCC cell line into a cell having a primary human hepatocyte phenotype; introducing a genome of a hepatotrophic virus into at least one of the hHCC cell line or the cell having primary human hepatocyte phenotype; contacting the cell culture with a sample of suspected of containing an antibody; maintaining the cell culture under conditions suitable for viral replication; and detecting the presence or absence of an effect of the sample upon viral replication; wherein a decrease in viral particle production in the presence of the sample as compared to the absence of the sample indicates the sample contains an antibody having antiviral activity. In some embodiments, the viral genome is introduced by adding infectious viral particles to the culture medium. In some embodiments, the infectious viral particles are added at day 1 of said culturing. In some embodiments, the viral genome is introduced into the hHCC cell line prior to said incubating.

The present disclosure provides methods for screening a candidate agent for the treatment of a lipoprotein mediated disease, the method comprising: incubating a cell culture comprising a human hepatocellular carcinoma (hHCC) cell line in a culture medium comprising human serum for at least 3 days, at least 5 days, and, in some embodiments, at least 14 days, wherein said incubating induces differentiation of the hHCC cell line into a cell having a primary human hepatocyte phenotype; contacting the cell culture with the candidate agent; and assaying the cell culture for the presence or absence of an effect of the candidate agent on the levels of lipoprotein secreted by the differentiated hHCC cell line as compared to a control sample; wherein an effect of the candidate agent on the levels of lipoprotein secreted by the differentiated hHCC cell line indicates that the candidate agent can be used for the treatment of the lipoprotein mediated disease. In certain embodiments, the cell culture is assayed for the presence or absence of an effect of the candidate agent on the levels of very low density lipoprotein (VLDL), low density lipoprotein (LDL), and/or high density lipoprotein (HDL) in the culture medium as compared to a control sample. In specific embodiments, the method is for the screening for a candidate agent for the treatment of atherosclerosis, wherein a decrease in VLDL or LDL or an increase in HDL indicates that the candidate agent can be used for the prevention or treatment of atherosclerosis.

The present disclosure provides methods for produced a cultured hepatocytic cell infected with a hepatotrophic microorganism (e.g., virus), the method comprising contacting a cultured hepatocyte cell with an infectious hepatotrophic microorganism in a culture medium comprising serum depleted of LDL-receptor binding lipoproteins, wherein contacting is for a time sufficient to provide for infection of the cultured hepatocyte cell with the hepatotrophic microorganism. In some embodiments, the cultured cells are primary hepatocytes or an immortalized hepatocyte cell line. In some embodiments, the cultured cells are differentiated hHCC cells. In some embodiments, the serum depleted of LDL-receptor binding lipoproteins is human serum depleted of LDL-receptor binding lipoproteins or fetal bovine serum depleted of LDL-receptor binding lipoproteins. In some embodiments, the infectious hepatotrophic microorganism is a hepatotrophic virus. In some embodiments, the hepatotrophic virus is hepatitis C virus or hepatitis B virus. In some embodiments, the hepatotrophic virus is a clinical isolate.

These and other features will be apparent to the ordinarily skilled artisan upon reviewing the present specification.

BRIEF DESCRIPTION OF THE DRAWINGS

FIG. 2A is a set of photographs showing cells grown in media supplemented with FBS (left panel) and HS (middle panel) as compared to human primary hepatocytes in culture (right panel). FIG. 2B is a graph showing the cell number for cell cultures maintained in FBS-containing media (closed circles) versus HS-containing media (open circles).

FIG. 6A: Viral titers from cells that were cultured in FBS, following infection with JFH virus produced from cells cultured in human serum or fetal bovine serum (JFH-HS, circles; JFH-FBS, squares). FIG. 6B: Viral titers from cells grown under different conditions (FBS, open circles, HS, closed circles) were infected with the same virus (JFH-HS). FIG. 6C shows the 1000 fold difference in viral titers between production of JFH-FBS in FBS cultured cells as compared to JFH-HS in HS cultured cells. FIG. 6D: Long term production of high viral titers in cells grown in human serum with infection at the time of transfer of cells from FBS-containing media to HS-containing media (open circles) or at 14 days after transfer from FBS-containing media to HS-containing media (closed circles). FIG. 6E: Illustrates viral titers of cells grown in primary hepatocyte medium with 2% HS (PHM, 2% HS) or DMEM with 2% HS (DMEM, 2% HS).

DETAILED DESCRIPTION OF EMBODIMENTS

Figure 1:
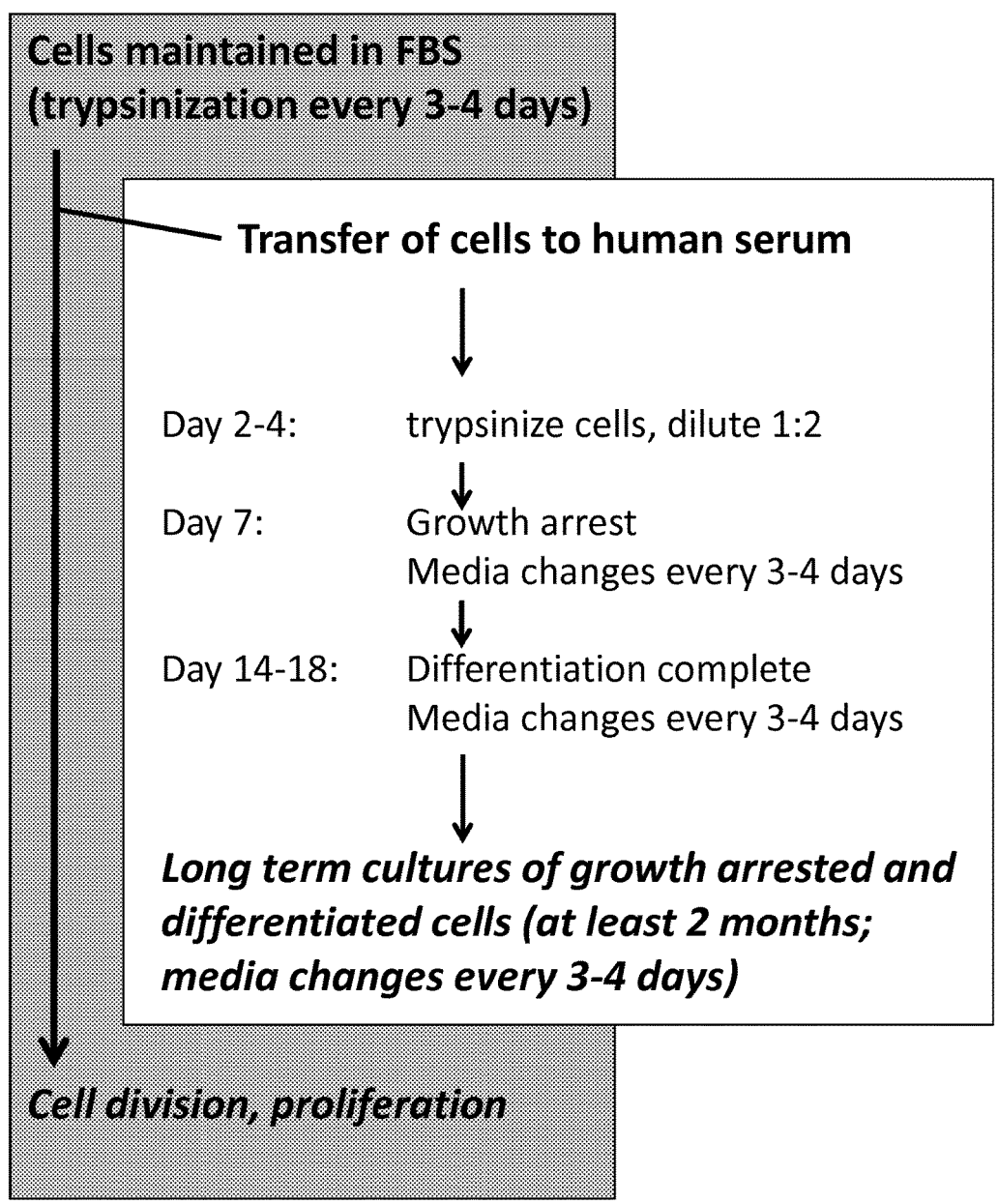
FIG. 1 is a flow chart showing an example of a time-line of culture conditions.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of such cells and reference to "the virus" includes reference to one or more viruses and equivalents thereof known to those skilled in the art, and so forth.

The publications discussed herein are provided solely for their disclosure prior to the priority date of the present application. Nothing herein is to be construed as an admission that the present invention is not entitled to antedate such publication by virtue of prior invention. Further, the dates of publication provided may be different from the actual publication dates which may need to be independently confirmed.

Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Definitions

A cell or cell culture is described as "undifferentiated" when a cell, or substantial proportion of cells and their progeny in a cell population, display morphological characteristics of undifferentiated parental cells, distinguishing them from differentiated cells having a desired phenotype different from the undifferentiated parental cell, e.g., a phenotype of a primary hepatocyte as described herein. It is understood that colonies of undifferentiated cells within the population will often be surrounded by neighboring cells that are differentiated.

A "growth environment" is an environment in which cells of interest will proliferate, differentiate, and/or mature in vitro. Features of the environment include the medium in which the cells are cultured, any growth factors or differentiation-inducing factors that may be present, and a supporting structure (such as a substrate on a solid surface) if present.

A "phenotypic marker" refers to an observable characteristic of a cell that is an indicator of a cell type. Phenotypic markers include biomarkers, morphological features, and physiological functions of a cell.

A "biomarker" as used herein generally refers to an organic biomolecule (e.g., a polypeptide) which is differentially present in cells of different phenotypic status (e.g., an undifferentiated hHCC cell as compared to a primary hepatocyte) or which is similar in a first cell to that of a second cell of having a known phenotypic status (e.g., a differentiated hHCC cell as compared to a primary hepatocyte). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a cell belongs to a phenotypic status of interest.

In assessment of phenotypic biomarkers on individual cells or cell populations, unless stated otherwise, the cell is said to be "positive" for a biomarker if the cell exhibits a detectable level of the biomarker significantly above a background or negative control level. Unless stated otherwise, a cell is said to be "negative" for a biomarker if expression of the biomarker is not significantly above a background or control level.

A cell is referred to as "genetically altered" or "genetically modified" when a polynucleotide has been transferred into the cell by any suitable means of artificial manipulation, or where the cell is a progeny of the originally genetically altered cell that has inherited the polynucleotide. The genetic alteration is said to be "inheritable" if progeny of the altered cell have the same alteration.

By "tissue culture adapted virus" is meant a virus that has been previously cultured in an in vitro cell culture so as to be selected for improved replication in an in vitro cell line, infectivity of an in vitro cell line, or both relative to the parent virus prior to culturing.

As used herein, an "adaptive mutation" in the context of an adapted virus refers to a genetic change that increases the ability of a virus to replicate, infect or both replicate and infect a target cell as compared to a replication competent virus that does not have the adaptive mutation.

By "genetically modified virus" is meant a virus produced from a viral genome genetically modified relative to a naturally occurring virus.

By "pseudotyped virus" is meant a virus having at least one viral protein (e.g., a coat protein) that is from a different origin (e.g., a different virus) than the viral genome contained in the virus.

"Primary cell culture" refers to an in vitro culture of cells obtained directly from a tissue (e.g., from liver) and are not immortalized (e.g., are not from a cancerous tissue or have not been transformed through culture to become immortalized).

The terms "polypeptide," "peptide" and "protein", used interchangeably herein, refer to a polymeric form of amino acids of any length, which can include biochemically modified or derivatized amino acids. The term includes fusion proteins, including, but not limited to, fusion proteins with a heterologous amino acid sequence, fusions with heterologous and homologous leader sequences, with or without N-terminal methionine residues; immunologically tagged proteins; and the like. "NH$_2$" refers to the free amino group present at the amino terminus of a polypeptide and "COOH" refers to the free carboxyl group present at the carboxyl terminus of a polypeptide.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Guidance for such substitutions can be drawn from alignments of amino acid sequences of polypeptides.

The term "polynucleotide" as used herein refers to a polymeric form of nucleotides of any length, either ribonucleotides or deoxyribonucleotides. This term includes double- and single-stranded DNA and RNA. It also includes known types of modifications, for example, naturally-occurring modifications such as methylation. Where the polynucleotide is non-naturally occurring, the polynucleotide can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

"Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transfected. It is understood that the progeny of a single parental cell may not necessarily be completely identical in morphology or in genomic or total DNA complement as the original parent, due to natural, accidental, or deliberate mutation.

"Replicon" refers to any genetic element, e.g., a plasmid, a chromosome, a virus, a cosmid, etc., that behaves as an autonomous unit of polynucleotide replication within a cell, i.e., capable of replication under its own control.

A "vector" refers to a replicon into which a selected polynucleotide can be inserted so as to bring about the replication and/or expression of the selected polynucleotide.

"Operably linked" refers to a juxtaposition wherein the components so described are in a relationship permitting them to function in their intended manner. A control sequence, such as a promoter, "operably linked" to a coding sequence is joined in such a way that expression of the coding sequence is achieved under conditions compatible with the control sequence.

"Transformation", as used herein, refers to the introduction of an exogenous polynucleotide into a host cell, irrespective of the method used for the insertion, for example, transduction, transfection, or electroporation. The exogenous polynucleotide may be maintained as a non-integrated vector, for example, a plasmid, or alternatively, may be integrated into the host genome.

"Isolated" refers to an entity of interest that is in an environment different from that in which the compound may naturally occur. "Isolated" is meant to include compounds that are within samples that are substantially enriched for the compound of interest and/or in which the compound of interest is partially or substantially purified.

By "purified" refers to a compound of interest (e.g., a polypeptide) that has been separated from components that accompany it in nature. "Purified" can also be used to refer to a compound of interest separated from components that can accompany it during manufacture (e.g., in chemical synthesis). In some embodiments, a compound is substantially pure when it is at least 50% to 60%, by weight, free from organic molecules with which it is naturally associated or with which it is associated during manufacture. In some embodiments, the preparation is at least 75%, at least 90%, at least 95%, or at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample that contains the compound. A substantially pure compound can also be obtained by recombinant or chemical synthetic production. Purity can be measured by any appropriate method, e.g., chromatography, mass spectroscopy, high performance liquid chromatography analysis, etc.

As used herein, the terms "determining", "assessing", "assaying", "measuring" and "detecting" refer to quantitative, semi-quantitative and qualitative determinations and as such, the term "determining" is used interchangeably herein with "assaying," "measuring," and the like. Where a quantitative determination is intended, the phrase "determining an amount" of an analyte and the like is used. Where either a quantitative and semi-quantitative determination is intended, the phrase "determining a level" of an analyte or "detecting" an analyte is used.

In Vitro Hepatocyte Cell Culture Methods and Compositions

The present disclosure provides methods of culturing a human hepatocellular carcinoma (hHCC) cell line under conditions sufficient to differentiate the hHCC cell line into a cell having a phenotype of a primary human hepatocyte. Examples of cells, culture medium and culture methods are described in more detail below.

Cells for Use in Culture Methods

Cells suitable for use the methods of the present disclosure to produce a cell having a primary human hepatocyte phenotype include human hepatocellular carcinoma (hHCC) cell lines. A "hHCC cell line" (also referred to as a human hepatoma cell line) refers to an immortalized cell line, and progeny thereof, where the immortalized cell line is of human hepatocyte origin (e.g., a cell line obtained by culturing a naturally-occurring cancerous human liver cell, e.g. hepatocellular carcinomas or hepatoblastomas). hHCC cell lines include, but are not necessarily limited to, HuH-7 cells (JCRB0403), a cell line derived from HuH-7 ("HuH-7-derived cells", e.g., Huh7.5; ATCC PTA-8561; U.S. Pat. No. 7,455,969), HuH-6 (JCRB0401) HepG2 (ATCC No. HB-8065); HepG2-derived cells (e.g., C3A (ATCC No. CRL-10741); and HepaRG™ cells (available from Life Technologes, Grand Island, N.Y., USA). By "derived cell" refers to a cell that is a subpopulation (or "subline") of a referenced parent cell, which has been isolated by selection of a desired phenotype (e.g., improved support of viral replication of a virus (e.g., a tissue culture-adapted virus (e.g., HCV)) relative to the parent cell). In one example, the hHCC cell is a HuH-7 cell or a HuH-7-derived cells (e.g., Huh7.5).

Cells suitable for use in the methods of the present disclosure can be used without the need for recombinant genetic modification, e.g., transfection with a construct, e.g., to facilitate increased viral titer production, or to facilitate differentiation to a phenotype of a primary human hepatocyte.

Culture Media

Culture media for maintenance and propagation of hHCC cells, including virally infected hHCC cells, can be any suitable culture media containing non-human serum, e.g., fetal bovine serum (FBS), also referred to as fetal calf serum (FCS), or synthetic serum (e.g., NuSerum®). In general, culture media for maintenance and propagation of hHCC cell lines can be selected so as to be compatible with the cell line.

Culture media for use in the methods of the present disclosure to induce differentiation of hHCC cells to have a phenotype of a primary human hepatocyte may be selected to as to be most compatible with the starting cell line used, but with substitution of human serum (HS) for non-human serum (e.g., in lieu of fetal bovine serum (FBS)).

In general, the culture medium comprises a carbon source, a nitrogen source, inorganic salts, trace nutrients, buffers and, optionally, antibiotics. The carbon source can be various sugar alcohols, polyols, aldol sugars or keto sugars including but not limited to arabinose, cellobiose, fructose, glucose, glycerol, inositol, lactose, maltose, mannitol, mannose, rhamnose, raffinose, sorbitol, sorbose, sucrose, trehalose, pyruvate, succinate or methylarnine or other substrates which may be determined by one skilled in the art.

The medium can contain a polyol or aldol sugar. In a more specific embodiment, the media comprises mannitol, inositol, sorbose, glycerol, sorbitol, lactose and arabinose as the carbon source at a concentration of about 0.1 hHCC to about 20.0% by weight. All of the carbon source(s) may be added to the medium before the start of culturing, or it may be added step by step or continuously during culturing. The culture media may also comprise a nitrogen source, suitable inorganic salts, and, as appropriate, various trace nutrients, growth factors and the like.

Examples of suitable supplemental carbon sources include, but are not limited to: other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol, inositol, mannitol and sorbitol.

Examples of suitable nitrogen sources include, but are not limited to: ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

Examples of suitable inorganic salts include, but are not limited to: salts of potassium, calcium, sodium, magnesium, manganese, iron, cobalt, zinc, copper, molybdenum, tungsten and other trace elements, and phosphoric acid.

Examples of appropriate trace nutrients, growth factors, and the like include, but are not limited to: coenzyme A, pantothenic acid, pyridoxine-HCl, biotin, thiamine, riboflavin, flavine mononucleotide, flavine adenine dinucleotide, DL-6,8-thioctic acid, folic acid, Vitamin Bi2, other vitamins, amino acids such as cysteine and hydroxyproline, bases such as adenine, uracil, uridine, guanine, thymine and cytosine, sodium thiosulfate, p- or r-aminobenzoic acid, niacinamide, nitriloacetate, and the like, either as pure or partially purified chemical compounds or as present in natural materials. In some embodiments, the culture medium contains uridine and/or cytidine in concentrations of less than 50 µM-200 µM each.

Examples of antibiotics used in cell cultures include, but are not limited to penicillin, neomycin, tetracycline, gentamicin, kanamycin, streptomycin and mixtures thereof.

Examples of suitable culture media include, but are not limited to, DMEM, DMEM/F-12, Leibovitz L-15 media, RPMI 1640, and primary hepatocyte medium (referred to herein as PHM). Suitability of additional culture media can be easily assessed, and the methods of the present invention are not limited to the specific type of cell culture media used in the culture, provided the media is suitable to support growth of the hHCC cell line and suitable for addition of human serum. The culture medium can be provided so as to contain no added non-human serum (e.g., no added fetal bovine serum).

In general, the human serum used in the methods and compositions of the present disclosure is obtained from a human subject by conventional methods. "Human serum" contemplates use of serum from an individual as well as pooled serum from multiple individuals. "Human serum" encompasses complete human serum, as well as subfractions thereof. Where the differentiated hHCC are to be used in production viral particles at high levels, the human serum subfraction contains human low density lipoproteins (LDL), or is supplemented with human LDL. Human serum can be used fresh or after storage (e.g., at −20 degrees Celsius). Human serum can be heat-inactivated prior to use.

The human serum may be obtained from a healthy human subject, e.g., a human subject who does not have a detectable infection by a pathogen (e.g., a pathogen to be cultured in the cells) and/or is naïve with respect to the pathogen (e.g., no anti-pathogen antibodies are present in the human serum). Use of human serum obtained from a healthy subject may be of particular interest where the culture of differentiated hHCC cells having a phenotype of a primary human hepatocyte is to be used in methods involving infection of the cells with a pathogen and/or propagation of a pathogen in cells (e.g., with HCV).

Human serum can be present in the culture media at any concentration suitable for culturing of a hHCC cell line and its differentiation to have a phenotype of a primary human hepatocyte. For example, human serum can be present at a concentration of from at least 1% (v/v), at least 2% (v/v), at least 5% (v/v), at least 8% (v/v), at least 10% (v/v) or more, and can have from about 1% (v/v) to 20% (v/v), or from about 2% (v/v) to 10% (v/v).

Methods of Culturing to Promote hHCC Cell Differentiation

In general, the culturing method of the present disclosure involves culturing a hHCC cell line in a culture medium comprising human serum under conditions sufficient to provide for induction of differentiation of the hHCC into a cell having a phenotype of a primary human hepatocyte. FIG. 1 provides an example of a culturing method of the present disclosure.

As noted above, prior to culturing in HS, the hHCC cells may be cultured in any suitable culture medium, which normally contains non-human serum or a non-human serum substitute (e.g., NuSerum®). hHCC cell cultures in FBS-containing medium can be subcultured (e.g., by trypsinization) as needed, e.g., every 3-4 days. Whether maintained n FBS-containing medium or during culture in HS-containing medium, cells are generally cultured under incubation conditions suitable for the hHCC cell line, e.g., 37° C., 5% $CO_2$.

Transfer of FBS-cultured hHCC cells to HS-containing medium can be accomplished by dissociation of FBS-cultured hHCC monolayers, and resuspension and plating of hHCC cells in HS-containing medium. Cultures of FBS-cultured hHCC cell monolayers can be dissociated using any suitable method, e.g., by treatment with trypsin). Where an enzyme such as trypsin is used to facilitate monolayer dissociation, the enzyme can be inactivated (e.g., with culture medium containing serum, e.g., FBS or HS). Dissociated cells are then centrifuged and cell pellets resuspended in HS-containing culture medium. Cells are then plated onto tissue culture plates at a suitable density, e.g., about 30% to 50%. Such can be achieved by, for example, plating 3-5 mls of a suspension of $10^6$ cells/ml on to a 75 $cm^2$ plate.

After culturing in HS-containing medium is initiated, cells need not be subcultured for the remainder of the life of the cell culture. Cell culture media is generally changed every 3 to 4 days, or every 2 to 4 days.

Optionally, within about 2 to 7 days, about 2 to 6 days, about 2 to 5 days, about 2 to 4 days, or about 2 to 3 days after plating in HS-containing medium (e.g., when cells cultured in HS-containing medium are at or near confluency), cell cultures can be subcultured ("split"), e.g., using standard techniques of monolayer dissociation (e.g., by treatment with trypsin followed by trypsin inactivation), centrifugation, resuspension in HS-containing culture medium, and plating onto tissue culture dishes. In general at this stage, if this optional subculture best results are achieved if the cells are diluted at no more than about 1:2 (i.e., no more than about 50% dilution) prior to replating. Although the methods of the present disclosure provide that HS-cultured cells can be divided in this manner for up to approximately 1 week after transition to HS-containing culture medium (again, with best results achieved if cells are not divided more than 1:2), trypsinization after about 10 days of culturing in human serum and replating did not provide best results, and was associated with cell culture death. The adverse impact of trypsinization after about 10 days may be reduced by plating of cells on to collagen-coated plates.

Without being held to theory, at about 7 days of culturing in HS-containing medium, the cells appear to enter growth arrest, at which point division of cells slows and generally stops as compared to growth in FBS-containing medium. (FIG. 1) The culture method can thus take this observation into account, and avoid subculturing of cells following initiation of growth arrest during culturing in HS-containing medium, e.g., no subculturing after about 7 days, about 8 days, about 9 days, or about 10 days of culturing in HS-containing medium.

As set out in the example of a method of the present disclosure in FIG. 1, and without being held to theory, following apparent growth arrest of cells at about 7 days of culture in HS-containing medium, hHCC cells begin to show evidence of differentiation toward the phenotype of a primary human hepatocyte. Within about 14 days, 15 days, 16 days, 17 days, or 18 days or more of culture in HS-containing medium, the culture contains cells that have completed differentiation into the phenotype of a primary human hepatocyte. In general, such differentiated cells cultures contain at least 75%, at least 80%, at least 85%, at least 90%, or at least 95% or more differentiated cells.

The culture conditions suitable for induction of the phenotype of a primary human hepatocyte in a hHCC generally involve culturing the hHCC in a suitable culture medium containing human serum (HS) (e.g., at least 2% vol/vol. HS) for a period of at least 7 days, usually more than 11 days, usually at least 14 days, at least 15 days, at least 16 days, at least 17, days at least 18 days, at least 19 days, at least 20 days, or at least 21 days, or more.

In general, the culture of hHCC cells in HS-containing culture medium can be performed without subculturing of cells more than one time or without subculturing within the first 7 days or within the first 10 days of culturing in HS-containing medium. "Subculturing" refers to dividing ("splitting") the cultured cell population so as to reduce cell density in the culture.

hHCC cells differentiated into the phenotype of a primary human hepatocyte can be sustained in culture for at least 1 month, or at least 2 months or more. Such long term cultures can be maintained without subculturing.

An example of a method of the present disclosure is described schematically in FIG. 1. For example, hHCC cells can be maintained in FBS-containing culture media, with subculturing (e.g., by trypsinization) every 3-4 days. hHCC cells are subcultured and transferred into culture medium containing HS. At day 2-4 after transfer to HS-containing media, the cells are optionally subcultured, with dilution at no more than 1:2. At day 7 after transfer to HS-containing medium, hHCC cells begin to show signs of growth arrest, e.g., arrest of cell division (i.e., cell number in the population does not significantly increase), cells do not aggregate (e.g., cells do not pile up on top of each other), can be maintained long term without the need to subculture). After this point the cells are not subcultured and the media is changed to fresh HS-containing media every 3-4 days. At about days 14-18 after transfer to HS-containing media, the hHCC cells appear to have completed differentiation into cells having the phenotype of a primary human hepatocyte. These cells are maintained in culture, with media changes to fresh HS-containing media, for at least 1 month, 2 months or more.

Compositions Comprising Differentiated hHCC Cells

The present disclosure provides cell populations comprising a differentiated hHCC cell having a phenotype of a primary human hepatocyte. For sake of brevity, cells differentiated from hHCC cells and having a phenotype of a human primary hepatocyte may also be referred to herein as "differentiated hHCC cells". By "phenotype of a primary human hepatocyte" is meant a cell characterized according to whether it expresses a phenotypic marker (e.g., biomarkers, physiological functions of the cell, and morphological features) characteristic of a primary human hepatocyte. The appearance and number of phenotypic markers (e.g., 2 or more, 3 or more, 4 or more or all of the biomarkers and/or morphological features and/or physiological features such as described below) depends upon the stage of differentiation of an hHCC cell toward a fully differentiated hHCC having a phenotype of a primary human hepatocyte.

Phenotypic markers of a phenotype of a primary human hepatocyte as provided below generally begin appear in hHCC after culturing in HS-containing medium for at least 7 days. Additional phenotypic markers, as well as increasing expression levels of a phenotypic biomarkers, are present with continued culturing of the hHCC in HS-containing medium (e.g., for at least 8 days, at least 9 days, at least 10 days, at least 11 days, at least 12 days, at least 13 days, or at least 14 days or more) as the hHCC progresses toward becoming a fully differentiated hHCC.

Phenotypic biomarkers characteristic of a primary human hepatocyte include expression of 2, 3, 4 or all of the biomarkers albumin, alpha1-antiTrypsin, and LxRα/NR1H3, as well as expression of claudin-1 and occludin, which are associated with formation of tight junctions. A phenotype of a primary human hepatocyte can be defined by being positive for expression of at least albumin and alpha1-antiTrypsin, where expression of each of these biomarkers at a level above a negative control level is indicative of a phenotype of a primary human hepatocyte (e.g., above a level of expression of albumin and alpha1-antiTrypsin when the hHCC is cultured in the absence of human serum, with or without DMSO, as discussed below). Additional phenotypic biomarkers characteristic of a primary human hepatocyte include LxRα/NR1H3, claudin-1, and occludin. Differentiated hHCC may be described as being positive for expression of at least 1, 2, or all 3 of LxRα/NR1H3, claudin-1, and occludin above a negative control level (e.g., above a level of expression of the hHCC cultured in in the absence of human serum, with or without DMSO, as discussed below).

Differentiated hHCCs having a characteristic of a primary human hepatocyte can be described in terms of differential expression of one or more phenotypic biomarker(s) relative that expressed by a negative control, e.g., the hHCC cultured in the absence of human serum (e.g., in the presence of a non-human serum such as FBS or adult bovine serum (ABS), which culturing may be with or without DMSO). Thus, for example, a level of expression of a phenotypic biomarker in hHCC cells cultured in non-human serum (e.g., FBS or ABS, with or without DMSO) are considered to be negative for expression of phenotypic markers of a primary human hepatocyte of albumin, alpha1-antiTrypsin, LxRα/NR1H3, occludin and claudin1 at a level characteristic of a primary human hepatocyte.

Differentiated hHCC cells having a phenotype characteristic of a primary human hepatocyte may be described as exhibiting differential expression of 1, 2, 3, 4 or more of albumin, alpha1-antiTrypsin, LxRα/NR1H3, claudin-1, and occludin, where the expression level of the biomarker in the differentiated hHCC is significantly greater than the expression level of the biomarker of the hHCC cultured in the absence of human serum, and may be at least 1.5-fold, 2-fold, 2.5-fold or greater in differentiated hHCC as compared to the hHCC cultured in the absence of human serum.

Phenotypic markers of a phenotype of a primary human hepatocyte include morphological features. Morphological features of primary human hepatocytes include granular appearance, polygonal (e.g., cuboidal) shape of cells, formation of tight junctions, and pavement like organization of cell population, with multinucleation also often a typical feature of a primary human hepatocytes.

Phenotypic marker of a phenotype of a primary human hepatocyte include cellular physiological features, e.g., cellular activities associated with a primary human hepatocyte. Physiological features of a phenotype of primary human hepatocyte include secretion of albumin, as well as uptake and utilization of lipids of low density lipoprotein (LDL).

Fully differentiated hHCC having a phenotype of a primary human hepatocyte can be described by any suitable combination of the phenotypic markers described herein, where the combination is sufficient to distinguish a primary human hepatocyte from cells that is not a primary human hepatocyte. In general, fully differentiated hHCC having a phenotype of a primary hepatocyte can be identified by being positive for expression of alpha1-antiTrypsin and albumin, and polygonal (e.g., cuboidal) cell shape. In fully differentiated hHCC, albumin and alpha1-antiTrypsin may be each expressed at a level that is not significantly lower than, and may about the same or greater than, a level of albumin and alpha1-antiTrypsin expression in a primary human hepatocyte cultured under the same conditions.

Fully differentiated hHCC having a phenotype of a primary human hepatocyte may also be optionally characterized by expression of one or both of the tight junction proteins claudin-1 and occludin. For example, fully differentiated hHCC having a phenotype of a primary human hepatocyte may express each of claudin-1 and occludin at a level that is not significantly lower than, and may about the same or greater than, that of a primary human hepatocyte cultured under the same conditions. Fully differentiated hHCC having a phenotype of a primary human hepatocyte may also be characterized by the morphological feature of the presence of tight junctions and/or by the physiological feature of the ability to uptake and utilize lipid of LDL.

Markers of a primary human hepatocyte phenotype can be detected using any suitable method. For example, markers can be detected using any suitable immunological technique—such as flow immunocytochemistry for cell-surface markers, or immunohistochemistry (for example, of fixed cells or tissue sections) for intracellular or cell-surface markers. For example, expression of a cell-surface antigen can be detected by binding of a specific antibody to the antigen in a standard immunocytochemistry or flow cytometry assay, optionally after fixation of the cells, and optionally using a labeled secondary antibody or other conjugate to amplify labeling.

The expression of gene product markers can also be detected at the mRNA level by Northern blot analysis, dot-blot hybridization analysis, or by reverse transcriptase initiated polymerase chain reaction (RT-PCR) using sequence-specific primers in standard amplification methods. Sequence data for particular markers can be obtained from public databases such as GenBank.

The present disclosure can provide a culture cell population comprising both undifferentiated and differentiated hHCC cells such that a proportion of cells in the population have the characteristics of a primary human hepatocyte. For example, such cell cultures can include those in which at least about 20%, at least 30%, at least 40%, at least 50%, at least 60%, at least 70%, at least 80%, at least 90%, at least 98% or more of the cells in the population are differentiated hHCC cells, e.g., which are positive for one, two, three, or more of any of the phenotypic markers and/or morphological markers characteristic of a primary human hepatocyte as described above. It may also be desirable to minimize the proportion undifferentiated hHCC cells in a cell population. In certain embodiments, differentiated hHCC cell populations have less than 15%, less than 10%, or less than 5% undifferentiated hHCC cells.

The methods of the present application can provide for large populations of hHCC differentiated cells having a phenotype of a primary human hepatocyte. Populations of at least $10^8$, $10^{10}$, or $10^{12}$ cells having a phenotype of a primary human hepatocyte can be produced.

Compositions of the present disclosure include cultured cell populations comprising cells having a phenotype of a human primary hepatocyte, wherein the cells are the differentiated progeny of an hHCC cell line; and a culture medium comprising human serum. In some embodiments, the cell culture has been continuously maintained for at least 7 days, at least 8 days, at least 9 days, at least 10 days, at least 11 days, at least 12 days, at least 13 days, at least 14 days, at least 15 days, at least 16 days, at least 17, days at least 18 days, at least 19 days, at least 20 days, or at least 21 days, or more. In some embodiments, the culture medium comprises from about 1% to 20% human serum, optionally from about 2% to 10% human serum. In some embodiments, the hHCC cell line is a HuH-7 or HuH-7-derived cell line. In some embodiments the cultured cells are adhered on a solid support (e.g., a well of a culture plate, a bead, and the like), where the solid support optionally comprises one or more extracellular matrix components, e.g., collagen (e.g., collagen Type I), to facilitate adherence of the cultured cells to the solid support.

Compositions of the present disclosure include cultured cell populations comprising differentiated hHCC cells which have been maintained in culture for at least 1 week, 2 weeks, 3 weeks, 4 weeks, 5 weeks, 6 weeks, 7 weeks, or 8 weeks or more.

Cells differentiated from hHCC cell lines exhibit a phenotype of a primary human hepatocyte, but, because they are derived from an hHCC cell line, can also be characterized as being differentiated progeny of the originating cell or cell line. Accordingly, the differentiated hHCC will have the same genome as the cells from which they are derived. This means that over and above any karyotype changes, the chromosomal DNA will be over 90% identical between the original parental hHCC cell line and the differentiated hHCC cells produced therefrom and having the phenotype of a primary human hepatocyte. Differentiated hHCC cells that have undergone genetic changes normally associated with culturing of the parental hHCC cell line under conventional culture methods, or which have been treated by recombinant methods to introduce a transgene or knock out an endogenous gene, are still considered to have the same genome as the line from which they are derived, since all non-recombinantly manipulated genetic elements are preserved. Differentiated hHCC cells and their parental hHCC cells can be identified as having the same genome by standard genetic fingerprinting techniques.

This characteristic can be valuable feature of the differentiated hHCC cells of the present disclosure. For example, use of the same hHCC cell line to generate differentiated hHCC cells can reduce variation between the populations of differentiated hHCC cells generated at different times.

Certain embodiments of the compositions of the disclosure include originating cells (such as a undifferentiated hHCC cell line, or an intermediate population) in combination with differentiated cells bearing characteristics of primary human hepatocytes. The two populations may either be in the same container (e.g., in coculture), in separate containers in the same facility, or in two different locations. The undifferentiated and differentiated cells may be present simultaneously or at a different time, such as when a culture of undifferentiated cells is caused to differentiate it its entirety into differentiated hHCC.

Methods and Compositions Using Culture Medium Containing Serum Depleted of LDL-Receptor Binding Lipoproteins The present disclosure also provides methods and compositions for use in infection of cultured cells with a hepatotrophic microorganism (e.g., hepatotrophic virus, hepatotrophic parasite (e.g., malaria), and the like). In general, the method involves exposing the cultured cells to a hepatotrophic microorganism in the presence of culture medium containing serum depleted of LDL-receptor binding lipoproteins, including LDL and VLDL, to facilitate infection of the cultured cells by the hepatotrophic microorganism such as a hepatitis virus, e.g., hepatitis A, B, C, D or E virus (HAV, HBV, HCV, HDV, HEV), and the like, cytomegalovirus (CMV). Where the hepatotrophic microorganism is a hepatitis virus, the virus can be on any genotype (e.g., HCV genotype 1 (e.g., genotype 1a, 1b, 1c), 2, 3, 4, 5, 6, and 7) and may be a naturally-occurring virus (e.g., a virus obtained from an infected primate, e.g., a clinical isolate obtained from an infected human), a tissue culture-adapted virus, a genetically modified virus, chimeric virus, or pseudotyped virus.

The cells for use in methods using serum depleted of LDL-receptor binding lipoproteins can be any suitable hepatocyte cell, such as primary hepatocytes, an immortalized hepatocyte cell line (e.g., an hHCC cells), and hHCC cells differentiated according to the methods disclosed herein to exhibit a phenotype of a primary human hepatocyte). The present method finds particular use in providing for infection of cultured hepatocyte cells (e.g., primary hepatocytes or immortalized hepatocyte cell lines, including hHCC cells differentiated to exhibit a phenotype of a primary human hepatocyte) with a clinical isolate of a hepatitis virus, e.g., a clinical isolate of HCV.

Serum depleted of LDL-receptor binding lipoproteins for use in the culture medium in these methods of the present disclosure can be prepared by any suitable method available in the art. Serum for use in the methods can be of human, bovine (e.g., fetal bovine) or any other suitable source. In one example, serum depleted of LDL-receptor binding lipoproteins is prepared by contacting the serum with a binding agent for lipoproteins that bind the LDL receptor, e.g., the human LDL receptor (e.g., an anti-LDL receptor binding lipoprotein antibody (e.g., a polyclonal or monoclonal antibody, an anti-VLDL antibody, an anti-LDL antibody, an anti-Apolipoprotein B antibody) or heparin) for a period of time sufficient to provide for binding to the binding agent, followed by recovering serum components that are not bound by the binding agent for use in the culture medium. By "serum depleted of LDL-receptor binding lipoproteins" is meant serum that is depleted of LDL-receptor binding lipoproteins relative to serum prior to treatment ("untreated serum"), and encompasses serum that is depleted of LDL-receptor binding lipoproteins by at least 20%, 30%, 40%, 50%, 60%, 70%, 80%, 90% or more relative to serum prior to depletion. In one embodiment, the serum depleted of LDL-receptor binding lipoproteins is not substantially depleted of HDL (which does not significantly bind the LDL receptor) relative to the serum prior to treatment.

In one embodiment, serum depleted of LDL-receptor binding lipoproteins is prepared by contacting the serum with heparin as a binding agent, where contacting is for a period of time sufficient to provide for binding of heparin-binding components in serum (e.g., LDL, VDL) to heparin, followed by recovering serum components that are not bound by heparin for use in the culture medium.

Sera for use in the present methods includes serum depleted of at least 25%, 30%, 40%, 50%, 60%, 70%, 80%, 90% or more of lipoproteins compared to serum prior to depletion, serum depleted of at least 25%, 30%, 40%, 50%, 60%, 70%, 80%, 90% of heparin-binding lipoproteins compared to serum prior to depletion, and/or serum depleted of at least 25%, 30%, 40%, 50%, 60%, 70%, 80%, 90% or more of ApoB compared to serum prior to depletion.

Methods of the present disclosure using lipoprotein-depleted serum (e.g., heparin-treated serum) involve infecting cells (e.g., an hHCC cell, primary human hepatocytes, or other cells susceptible to infection by a hepatotrophic microorganism) with a hepatotrophic microorganism, where the cells are cultured in medium containing lipoprotein-depleted serum. Following infection, cells can be transitioned to any suitable culture medium (e.g., HS-containing medium for hHCC cells where differentiation is desired or maintenance of differentiated hHCC cells).

Uses

The methods and compositions of the present disclosure can be used in a variety of ways such as, but not limited to, production of viral particles (e.g., as in viral vaccine production), study of hepatocyte function, and screening methods. Examples of uses are described below in more detail.

Viral Particle Production

The methods and compositions of the present disclosure can be used in production of viral particles, particularly viral particles of a hepatotrophic virus such as a hepatitis virus, e.g., hepatitis A, B, C, D or E virus (HAV, HBV, HCV, HDV, HEV), and the like, cytomegalovirus (CMV). The virus can be on any genotype (e.g., HCV genotype 1 (e.g., genotype 1a, 1b, 1c), 2, 3, 4, 5, 6, and 7) and may be a naturally-occurring virus (e.g., a virus obtained from an infected primate, e.g., an infected human, often referred to as a "clinical isolate"), a tissue culture-adapted virus, a genetically modified virus, or pseudotyped virus.

Virus particle-producing, differentiated hHCC cells of the present disclosure can be accomplished using any suitable method. For example, a viral genome can be introduced into cells by infection, electroporation, transfection, and the like. In some embodiments, the hHCC cells and/or the differentiated hHCC cell are not modified by recombinant techniques so as to provide a genomically integrated viral genome. In some embodiments, the hHCC cells and/or the differentiated hHCC cells are not genetically modified to include a genomically integrated viral genome operably linked to a promoter that is not native to the viral genome.

Viral genomes can be introduced into hHCC cells prior to differentiation in HS-containing medium, at the time of transition from FBS-containing medium to HS-containing medium, during differentiation by culturing in HS-containing medium (e.g., at 1, 2, 3, 4, 5, or 6 days after transition to HS-containing medium), or after growth arrest and/or differentiation to a phenotype of a primary human hepatocyte (e.g., at 7, 8, 9, 10, 11, 12, 13, 14 days or more after transition to HS-containing medium).

Where viral genomes are to be introduced by infection, infection can be conducted in culture medium containing lipoprotein-depleted (e.g., heparin-treated) serum (e.g., human serum, fetal bovine serum) as described above. Optionally, following infection cells can be transitioned to HS-containing medium, e.g., to provide for differentiation of hHCC cells and/or to facilitate cell viability. In one embodiment, undifferentiated or differentiated hHCC cells are cultured in medium containing lipoprotein-depleted serum for a period of time to allow for infection of viral particles added to the cells. Following the infection period, the culture medium is replaced with HS-containing medium and the cells cultured for a period of time to provide for differentiation of hHCC cells, continue differentiation of hHCC cells, and/or provide for maintenance of differentiated hHCC cells and provide for viral particle production.

The present disclosure provides cultures of differentiated hHCC cells comprising at least $10^5$, at least $10^6$, at least $10^7$ at least $10^8$, or at least $10^9$ or more viral particles per milliliter of culture medium. The present disclosure further provides such viral particle-producing cultures that can be maintained for at least 1 week, 2 weeks, 3 weeks, 4 weeks, 5 weeks, 6 weeks, 7 weeks, or 8 weeks or more.

Viral particles produced from hHCC cells cultured in HS exhibit structural features that distinguish such from viral particles produced in hHCC cells cultured in non-human serum (e.g., in FBS). For example, when produced in differentiated hHCC cells cultured in HS, viral particles have an average lower density than when produced from the hHCC cells cultured in FBS. For example, when HCV particles are produced in FBS-cultured hHCC cells, about 75% of the viral particles have a density greater than about 1.16 g/ml. In contrast, when HCV particles are produced in HS-cultured hHCC cells, the HCV particles are of a lower average density, with only about 25% of the HCV particles in the population having a density of greater than 1.16 g/ml. In addition, HCV particles produced from HS-cultured hHCC cells are associated with ApoB, with usually at least about 50%, at least about 60%, at least about 70%, at least about 80%, or at least about 90% or more of the HCV particles in the viral particle population produced being ApoB-associated.

Viral particles produced from the differentiated hHCC cells can be used in a variety of ways. For example, the viral particles produced from the differentiated hHCC cells can be isolated from the cell culture medium, and formulated so as to be suitable for administration as a vaccine. The viral particles can be used in research settings, e.g., for infection of animal models, such as a human chimeric mouse model. The differentiated hHCC cell populations also provide a research tool for use in study of viruses, especially hepatotrophic viruses.

Assays

The differentiated hHCCs of the present disclosure find use in a variety of assays. For example, the differentiated hHCCs can serve as a model of human hepatocytes, and thus a model of liver function and disease (for example, carcinogenesis, steatosis (fatty liver disease)). Other uses include studies of lipoprotein metabolism and secretion, and metabolic studies, both of biological intermediates as well as xenobiotic compounds (e.g., oxidation by cytochrome P450).

Assays using the differentiated hHCCs of the present disclosure can involve, for example, assessing the effect of an agent on cells having a phenotype of a primary human hepatocyte, e.g., to assess the effect of an agent on human hepatocyte function (e.g., to assess liver toxicity of an agent); to assess metabolism of an agent by a human hepatocyte; study mechanisms involved in hepatocyte function; and the like. The differentiated hHCC cells can be used to screen for agents (such as solvents, small molecule drugs, peptides, polynucleotides) and/or environmental conditions (such as culture conditions or manipulation) that affect the characteristics of cells having a phenotype of a human primary hepatocyte.

Assessment of activity of an agent (e.g., a candidate agent) generally involves contacting a differentiated hHCC cells with the agent, either alone or in combination with other agents (e.g., drugs having a known activity). After incubation for a sufficient amount of time, an appropriate assay is conducted to detect the effect, if any, of the candidate agent on the differentiated hHCC cells (e.g., by assessing a change in cell morphology, cell function, change in a marker of a phenotype of a human primary hepatocyte). The presence or absence of an effect of the agent on the phenotype is detected and analyzed, e.g., by comparing to a control (e.g., by comparison to the phenotype in the absence of the agent and/or by comparison to the phenotype in the presence of an agent having a known effect on a liver cell).

For example, where the assay is to assess an effect of a candidate agent on lipoprotein metabolism, the assay can involve detecting a change in a phenotypic marker, e.g., a morphological change (e.g., the presence or absence of a change in lipid organization in the differentiated hHCC cell (e.g., as indicated by the presence or absence of lipid droplets and/or a change in the pattern of such lipid droplets)) or a change in a biomarker, such as a lipoprotein or lipid (e.g., a change in a level of a lipoprotein or a lipid). in the presence of the candidate agent compared to the absence of the candidate agent. A change in the phenotypic marker in the presence of the candidate agent as compared to the absence of the agent indicates the candidate agent has an effect on lipoprotein metabolism.

In one aspect, provided herein is a method for assessing the effect of a candidate agent on lipoprotein secretion of any of the differentiated hHCC cells provided herein. As discussed in the Examples below, human hepatocellular carcinoma (hHCC) cell line cultured in a culture medium comprising human serum for at least 3-5 days or more secrete lipoprotein (e.g., VLDL, LDLs, HDLs). At 14 days or more of culturing in culture medium comprising human serum, hHCC cells secrete lipoproteins at levels that closely resemble those secreted by primary human hepatocytes in culture, and also closely resemble lipoprotein levels found in human serum. Thus, the secreted lipoprotein profile of hHCC cells cultured in human serum is similar to that of the profile of lipoproteins secreted by primary human hepatocytes and to that of the lipoprotein profile found in human serum. As such, a change in the levels of lipoprotein secretion in the presence of a candidate agent as compared to the absence of the agent indicates the candidate agent has an effect on lipoprotein secretion.

In certain embodiments, the method includes the steps of incubating a cell culture comprising a human hepatocellular carcinoma (hHCC) cell line in HS-containing media for more than 14 days. The hHCC cell line can be cultured in any HS-containing media described herein for 3 days or more. In certain embodiments the human hepatocellular carcinoma (hHCC) cell line is cultured in the HS-containing media for 3, 4, 5, 6, 7, 8, 9, 10, 11, 12, 13, 14, 15, 16, 17, 18, 19, 20, 21, 22, 23, 24, 25, 26, 27, 28, 29, or 30 or more days prior to contact with the candidate agent.

After culturing the hHCC cell line for a selected time period (e.g., to provide for a desired secreted lipoprotein profile), the cell line is then contacted with the candidate agent. Candidate agents include, but are not limited to, synthetic, naturally occurring, or recombinantly produced molecules (e.g., small molecule; drugs; polynucleotides; polypeptides; peptides; antibodies; endogenous factors present in eukaryotic or prokaryotic cells (e.g., polypeptides, plant extracts, and the like)); etc.). Candidate agents include agents of numerous chemical classes, though typically they are organic molecules, preferably small organic compounds having a molecular weight of more than 50 and less than about 2,500 daltons. Candidate agents include biomolecules such as, but not limited to: antibodies, peptides, saccharides, fatty acids, steroids, purines, pyrimidines, derivatives, structural analogs, nucleic acid inhibitors or combinations thereof.

The method can involve administering varying amounts of the candidate agent (from no agent to an amount of agent that approaches an upper limit of the amount that can be delivered within toxicity limits for cultured cells), and may include delivery of the agent in different formulations. The agents can be administered singly or can be combined in combinations of two or more, e.g., where the effect of a candidate combination drug therapy is to be assessed.

After incubation for a sufficient amount of time with the candidate agent, an appropriate assay is conducted to detect the effect, if any, of the candidate agent on the differentiated hHCC cells to secrete lipoproteins. In certain embodiments, the method includes the step of assessing the level of lipoproteins (e.g., VLDL, LDLs, and/or HDLs) in the HS-containing media. Levels of lipoproteins that are secreted by the hHCC cells can be assessed by any suitable method. For example, the levels of secreted lipoproteins can be assessed by assaying the media collected from the cultured hHCC cells to obtain a lipoprotein profile (a measurement of HDL, LDL, and/or VLDL cholesterol and triglyceride levels). Lipoprotein profiles can be obtained, for example, using ultra-centrifugation or by liquid chromatography techniques. See, e.g., Brousseau et al. (1993) Clinical Chemistry 39(6): 960-964. In certain embodiments, the lipoprotein profile is obtained by isolating the media used to culture the hHCC cells and separating the lipoproteins from the media using size exclusion fast protein liquid chromatography. Lipid content (e.g., cholesterol or triacylglycerol) can be subsequently measured by any suitable lipid detection method, including fluorescence-based lipid detection methods. See, e.g., Yang et al. (2012) Chem Phys Lipids 165(2): 133-41.

The presence or absence of an effect of the candidate agent on lipoprotein secretion is determined by comparison to a control sample (e.g., a control lipoprotein profile obtained from media of hHCC cells not contacted with the agent). In such embodiments, a difference in the lipoprotein levels in the presence of a candidate agent as compared to the control sample indicates the candidate agent has an effect on lipoprotein secretion. Any suitable sample can serve as a control sample for comparison to the levels of lipoprotein obtained from the hHCC cell line contacted with the candidate agent. In specific embodiments, the control sample is a lipoprotein profile obtained from a human hepatocellular carcinoma (hHCC) cell line cultured in the HS-containing media under the same conditions as the sample that is tested and in the absence of the candidate agent. In other embodiments, a comparison is made to a lipoprotein profile from a sample contacted with an agent having a known effect on hepatocyte lipoprotein secretion.

Such methods can be useful, for example, in screening for therapeutic agents for use in the treatment of lipoprotein mediated diseases and conditions, including, but not limited to dyslipidemia, hypolipidemia, hyperlipidemia, hypolipoproteinemia, hyperlipoproteinenemia, tangiers disease, hyperalphalipoproteinemia, hypoalphalipoproteinemia, coronary heart disease (CHD), cerebrovascular disease (CVD), atherosclerosis, thrombosis, and stroke. In specific embodiments, the method is for the prevention or treatment of atherosclerosis. In such embodiments, a decrease in VLDL or LDL or an increase in HDL in the culture medium as compared to the control sample is indicative that the candidate agent can be used for the prevention or treatment of atherosclerosis.

Where the assays is to assess metabolism of a drug, the method generally involves contacting a culture of differentiated hHCC cells having a phenotype of a human primary hepatocyte with a drug for a period of time sufficient for production of metabolites of the drug (if any), and assaying for metabolites of the drug (e.g., in the culture supernatant). Drug metabolites can be detected using methods available in the art. The metabolite can be subjected to further analysis, e.g., to identify the structure of the metabolite.

Where the assay is to assess toxicity of an agent on human hepatocytes, the method generally involves contacting a culture of differentiated hHCC cells having a phenotype of a human primary hepatocyte with an agent with an agent, and detecting a change in a phenotypic maker (e.g., a morphological change and/or a change in a biomarker indicative of toxicity, e.g., a change in a level of transaminase). Detection of a change in the presence of the agent as compared to the absence of the agent (e.g., an increase in transaminase in the cell medium in the presence of the agent and/or an increase in an phenotypic marker of cell death (e.g., a phenotypic marker of apoptotic cell death, necrotic cell death (e.g., TUNEL, caspase)) is an indicator of toxicity of the agent for the differentiated hHCC cells).

Where the differentiated hHCCs are cultured with a hepatotrophic microorganism (e.g., a hepatotrophic virus such as HCV, HBV), the assays can involve study of entry, replication, and, in the context of viruses, viral particle production. The assays can also provide for screening for anti-hepatotrophic pathogen agents, e.g., antiviral agents.

For example, where the assay is to screen for antiviral agents, the assay can generally involve incubating the differentiated hHCC cells in the presence of a viral genome with at least one test candidate agent, and detecting the presence or absence of an effect on the virus. Such can be accomplished by, for example, assaying viral replication. Assaying viral replication can be accomplished by, e.g., assessing levels of viral particles (e.g., viral titers), detecting viral nucleic acid, and the like. For example, where the differentiated hHCC cells are infected with HCV, levels of HCV may be assessed by measuring viral titers, measuring HCV RNA quantitatively, measuring HCV viral particles (e.g., by detection of core proteins, e.g., by immunoassay), by microscopy, and the like Inhibition of virus production viral replication can be due to, for example, inhibition of viral replication at the nucleic acid level, inhibition of viral particle production, and/or inhibition or viral entry into cells. A decrease in viral replication in the presence of the candidate agent as compared to the absence of the candidate agent indicates the candidate agent has antiviral activity.

Screening methods for antiviral agents can be adapted to screen for antiviral activity of an antibody, e.g., to assay for antibodies that neutralize virus by, for example, inhibition viral infectivity of a differentiated hHCC. Such antibodies may be a polyclonal or monoclonal antibody. In on embodiment, the antibodies to be screened are present in a biological samples obtained from a subject exposed to a virus (e.g., HCV) or to whom a vaccine (e.g., candidate vaccine) has been administered. The biological sample can be, for example, blood or a fraction thereof, e.g., suspected of containing antiviral antibodies. In one embodiment, the differentiated hHCC cells are infected with a clinical viral isolate. The assay can involve comparing viral replication in the presence of the antibody or sample of suspected of containing the antibody, where a decrease in viral replication in the presence of the antibody or the sample is an indicator of antiviral activity. Where the biological sample is from a subject post-immunization, the antiviral activity of the post-immunization sample may be compared to antiviral activity of a pre-immunization biological sample (e.g., from the same subject).

Any of a variety of candidate agents can be screened. "Candidate agents" is meant to include synthetic, naturally occurring, or recombinantly produced molecules (e.g., small molecule; drugs; polynucleotides; polypeptides; peptides; antibodies; endogenous factors present in eukaryotic or prokaryotic cells (e.g., polypeptides, plant extracts, and the like)); etc.). Candidate agents encompass numerous chemical classes, though typically they are organic molecules, preferably small organic compounds having a molecular weight of more than 50 and less than about 2,500 daltons. Candidate agents can also include biomolecules such as, but not limited to: antibodies, peptides, saccharides, fatty acids, steroids, purines, pyrimidines, derivatives, structural analogs or combinations thereof.

Candidate agents can be obtained from a wide variety of sources including libraries of synthetic or natural compounds. For example, numerous methods are available for random and directed synthesis of a wide variety of organic compounds and biomolecules, including expression of randomized oligonucleotides and oligopeptides. Libraries of natural compounds in the form of bacterial, fungal, plant and animal extracts are available or readily produced. Libraries of antibodies can be produced by methods available in the art. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The assays method can involve administering varying amounts of the candidate agent (from no agent to an amount of agent that approaches an upper limit of the amount that can be delivered within toxicity limits for cultured cells), and may include delivery of the agent in different formulations. The agents can be administered singly or can be combined in combinations of two or more, e.g., where the effect of a candidate combination drug therapy is to be assessed.

It will be appreciated that the assay can be conducted in a variety of formats, and that the order of contacting the differentiated hHCC cells with the virus and the candidate agent can be varied. For example, the differentiated hHCC cells can be infected virus prior to contacting with the candidate agent; alternatively, the differentiated hHCC cells can be contacted with the candidate agent prior to exposure to infectious viral particles.

The agent (e.g., candidate agent, drug, and/or microorganism (e.g., virus)) can be added to the culture medium at the time of transition of hHCC cells to HS-containing medium, during differentiation of hHCC cells, or after differentiation of hHCC cells into a phenotype of a human primary hepatocyte.

Kits

Kits of the present disclosure can include hHCC cells, differentiated hHCC cells having a phenotype of a human primary hepatocyte, or both. The kit can optionally include culture medium components, e.g., culture media (e.g., without serum or containing human serum), human serum for use in the culture, and the like). For example, the kit can include primary hepatocyte medium (such as described in detail in the Examples below), with or without human serum. The various components of the kit may be present in separate containers or certain compatible components may be pre-combined into a single container, as desired.

Kits can include instructions for using the components of the kit to practice a method of the present disclosure. The instructions are generally recorded on a suitable recording medium, such as paper, plastic, electronic storage, medium, and the like. For example, the instructions may be present in the kits as a package insert, in the labeling of the container of the kit or components thereof (e.g., associated with the packaging), etc. In other embodiments, the instructions are present as an electronic storage data file present on a suitable computer readable storage medium, e.g. compact disc-read only memory (CD-ROM), digital versatile disk (DVD), diskette, etc. In other examples, the instructions provided do not contain many or all assay details, but rather provide direction as to a remote source for obtaining detailed instructions, e.g. via the internet.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Materials and Methods

The following methods and materials are used in the Examples below.

Standard Culture Conditions (for Cell Proliferation Prior to Culturing in Human Serum).

HuH-7 (JCRB403) cells are available from the Japanese Collection of Research Resources—Cell bank (JCRB Cell bank). Huh7.5 cells were a kind gift of Dr. C. Rice. Both cell line were maintained (prior to culturing in human serum) according to the protocols described. In short, Huh7.5 or HuH-7 cells were maintained in culture medium containing DMEM/10% fetal bovine serum (FBS)/penicillin/streptomycin with trypsinization and splitting every 3 to 4 days. After approximately 20-30 passages, cells were discarded, and a new vial was thawed.

Since the use of human serum results in growth arrest of cells, cell cultures were normally maintained FBS containing media (DMEM/10% FBS/penicillin/streptomycin, as described above).

Infection of Cells with JFH-1 Virus.

JFH-1 virus (JFH) was obtained from Dr. T. Wakita. Two days prior to infection, cells were replated at 30% density. After infection for 4 hours, cells were washed and cultured in either FBS or HS containing as appropriate.

Infection of Chimeric Mice.

Chimeric SCID/uPA mice transplanted with human hepatocytes (see, e.g., WO 01/67854) were infected as described previously (Steenbergen et al. (2010) *Am J Physiol Gastrointest Liver Physiol* 299: G844-854; Mercer et al. (August 2001) *Nat. Med.* 7(8):927-33. Infection was accomplished using 100 µl of tissue culture supernatant from JFH-infected cells or serum from HCV-infected patients.

HCV titers and human albumin (hAlb) in the serum of the mouse model chimeric mice was determined by quantitative PCR and ELISA respectively.

Visualization and Quantitation of Lipid Droplets by Immunofluorescence.

Cells were grown on coverslips and either cultured in FBS or HS. Cells were stained with Bodipy 493/503 (Invitrogen) according to the supplier's instructions in order to visualize lipid droplets. The quantity of neutral lipid staining was visualized using a fluorescence microscope. Images of the Bodipy 493/503 staining under different cell culture conditions were taken using identical microscope and exposure settings. The amount of fluorescence was quantitated using ImageJ software (National Institutes of Health). Data were collected in 3 independent experiments, with 4-8 microscopic fields measured per condition. Background- and auto-fluorescence was negligible.

Distribution and shape of lipid droplets were examined in separately stained samples under identical microscopy settings, but with optimized exposure for each individual condition.

Sucrose Gradients/Density Centrifugation.

Sucrose density-gradient ultracentrifugation analysis was performed as previously described (Zhong et al. (2005) Proc Natl Acad Sci USA 102: 9294-9299). Supernatants from HCV-infected cells were centrifuged at 300 g for 5 min to remove cellular debris in 1 ml of THE buffer (50 mM Tris HCl, pH 8; 100 mM NaCl; 1 mM EDTA) containing protease inhibitors (RocheApplied Science, Indianapolis), loaded onto a 20-60% sucrose gradient (12.5-ml total volume), and centrifuged at 120,000 g for 16 h at 4° C. in a SW41Ti rotor (Beckman). Fractions of 0.5 ml each were collected from the top of the gradient, and the titer in each fraction was determined by quantitative RT-PCR as described below. The density of each fraction was determined by determining weight of a known volume.

Immunoprecipitation of ApoB Containing Particles.

Immunoprecipitation experiments were essentially performed as previously described (Steenbergen et al. (2010) Am J Physiol Gastrointest Liver Physiol 299: G844-854). Serum or cell culture supernatant samples (50 µl) with titers of at least $10^5$ RNA copies/ml were incubated overnight with 7.5 µl anti ApoB antibody (Chemicon AB742, goat anti human apolipoprotein B; cross-reacts with human, mouse and bovine ApoB), at 4° C. while rotating. Protein G slurry (20 µl, GE healthcare, Protein Sepharose 4 fast flow) was added to each sample and incubated for a minimum of 1 hour on a rotator. The Protein G complexes were precipitated at 14000 g in a microfuge. The pellets were washed once with PBS and viral RNA was isolated directly from the pellets (QiaAmp Viral RNA kit, Qiagen) and analyzed by quantitative RT-PCR. Samples containing high amounts of immunoglobulins (like patient serum) were pre-cleared with protein G beads, prior to immunoprecipitation, to ensure quantitative immunoprecipitation of the ApoB complexes. To ensure that the Protein G beads did not bind HCV or HCV complexes directly, we incubated HCV containing mouse serum with Protein G Sepharose beads in the absence of anti-ApoB antibodies. The HCV titers in the precipitate of these samples were negligible.

Quantitative RT-PCR of Hepatocyte Markers.

RNA was isolated from cells using Trizol, according to the instructions of the manufacturer. cDNA was produced from the RNA using Quantitect Reverse Transcription kit (Qiagen). Gene specific primer-probe sets were designed by Applied Biosystems. An Applied Biosystems 7900HT Fast Real-Time PCR system was used for the quantitation of gene products. Gene expression was calculated relative to HPRT according to Pfaffl (Pfaffl M W. *Nucleic Acids Res* 29: e45, 2001).

Primary Hepatocyte Cultures:

Frozen human primary hepatocytes were either purchased from Invitrogen, or isolated in-house as described previously (Mercer et al, 2001 Nat Med. 7 927-933). Isolated cells were pretreated with HypoThermosol HTS-Purge (BioLife Solutions), resuspended in Cryostor CS10 (BioLife Solutions) and cooled in a controlled rate freezer at the rate of 1° C. per minute until −40° C. Cells were then stored in liquid nitrogen. Cells were thawed and resuspended in pre-warmed primary hepatocyte medium (DMEM, 1.2 µg/ml insulin, 11 µM hydrocortisone hemisuccinate, 15 mM Hepes, penicillin/streptomycin, 200 mmol glucose, 2% human serum) and plated on Collagen type I coated plates (Millicoat 6 well plates, Millipore at a density of 1 million cells per well. After 12-18 hrs the tissue culture media was refreshed to remove unattached cells. Cells were used within 3 days after plating.

FPLC analysis of secreted lipoproteins: Size-exclusion fast-protein liquid chromatography (FPLC) was used to separate lipoprotein particles secreted by cultured Huh7.5 cells into media. In this system, the largest particles eluted first from the column (VLDL) followed by LDL and HDL sized particles. After separation, triacylglycerol (TG, also referred to as tryglyceride) or cholesterol content was determined in-line.

To prepare samples, cells were washed extensively with serum free OptiMEM (Gibco/Invitrogen) to remove lipoproteins present in the serum containing media. The last wash was collected and served as a baseline measurement. Cells were then placed in serum free OptiMEM overnight. The following day, media was collected and cellular debris was removed by centrifugation (300 g, 10 minutes). Media was then concentrated using a centrifugal filter unit (Amicon Ultra-100, Millipore). Concentrated media (65 µl) was injected into an Agilent 1200 HPLC instrument equipped with a Superose 6 10/300 FPLC column. In-line assays for total cholesterol and TG (Infinity Cholesterol and Triglyceride reagents, Thermo Scientific) were performed at 37° C. using a post-column reaction. Reaction products were monitored in real-time at 500 nm and analyzed using Agilent Chemstation software. All lipoproteins contain both TG and cholesterol. However, VLDL, is rich in TG and has little cholesterol, whereas HDL is rich in cholesterol and has little TG. Therefore, cholesterol profiles are more suitable to detect differences in secreted HDL levels, whereas TG profiles are more suitable to analyze VLDL levels.

Example 1: Growth and Appearance of Huh7.5 Cells Cultured in Human Serum

FIG. 1 provides a flowchart showing an example of the steps used in culturing of cells in human serum (HS) to provide for differentiated cells. Huh7.5 cells previously maintained in FBS-containing culture medium were trypsinized to facilitate dissociation of monolayers. Trypsin was inactivated with DMEM/10% FBS. Cells were then centrifuged at 300 g, and cell pellets were resuspended in DMEM/2% HS/penicillin/streptomycin and plated at a density of 30-50%. At confluency (typically after 2 days of incubation) cells were trypsinized once more, and then plated at a density of 50%. From this point on, cells were cultured without further splitting and allowed to form confluent layers of undividing cells. Optionally, cells cultured in human serum can be divided for up to approximately 1 week, provided they are not divided more than 1:2. However, repeated trypsinization after 10 days of culturing in human serum resulted in loss of viability of the cell cultures, with death of 80-90% or more of cells.

Figure 2A:
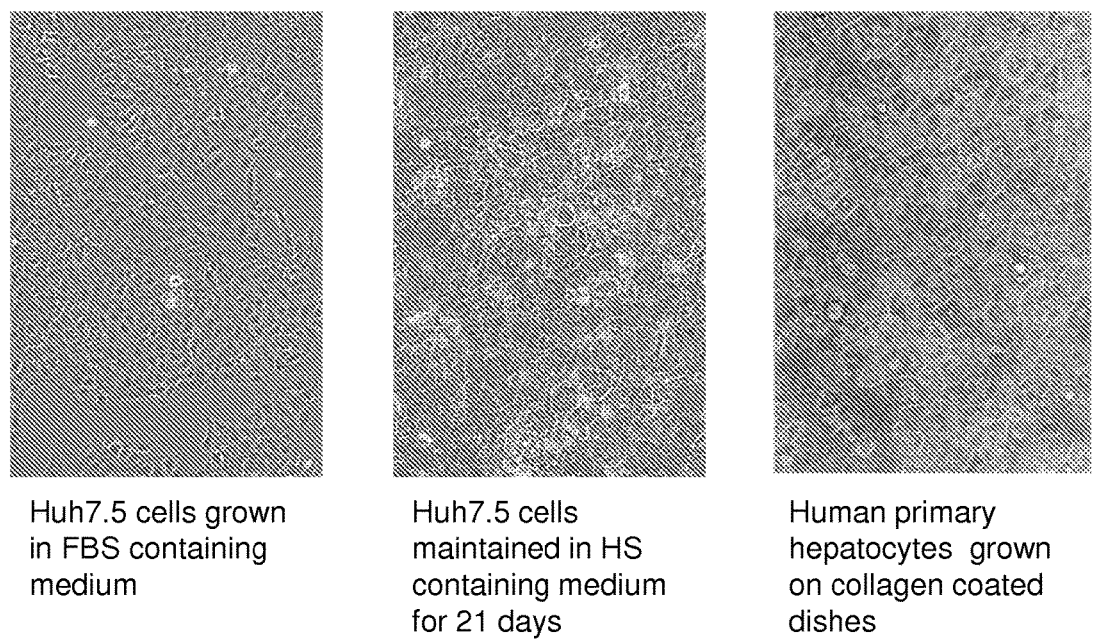
FIGS. 2A-2B illustrate the differences in appearance and growth of cells in culture medium containing fetal bovine serum (FBS) versus human serum (HS).

Huh7.5 cells grown in media supplemented with human serum (HS), instead of fetal bovine serum (FBS), underwent a series of morphological changes, and were maintained as confluent layers for over two months, without the further need for splitting. HS-cultured cells became organized in a pavement like structure, formed tightly packed monolayers that were very strongly attached to the tissue culture substrate. After approximately one week, cell division slowed down in cells cultured in HS-containing media, and eventually underwent contact inhibition and became growth arrested. Similar to primary hepatocytes in culture (right panel), HS-cultured cells were mono- or binucleated and had a granular appearance (FIG. 2A, middle panel) as compared to FBS-cultured cells (FIG. 2A, left panel). After approximately 14-18 days in HS cell size increased significantly.

Figure 2B:
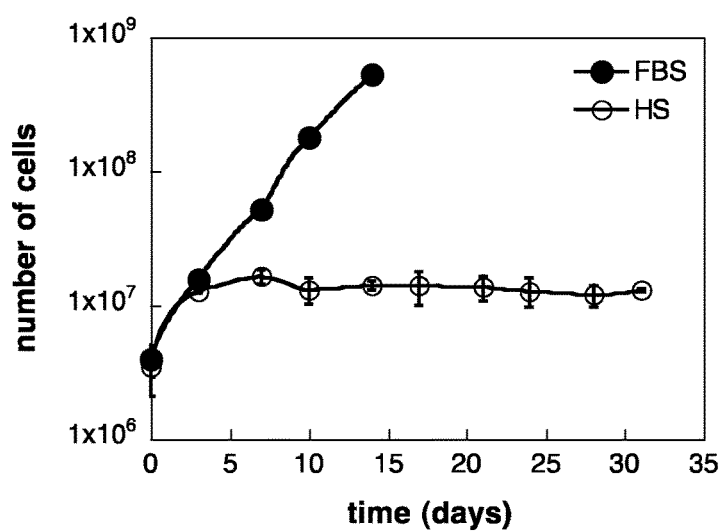

To examine the apparent growth arrest effect of culturing in HS, cell numbers where counted in a three-week time span after initial plating in HS-cultured cells and FBS-cultured cells. As shown in FIG. 2B, growth of cells cultured in HS-containing medium was significantly slowed as compared to growth in FBS-containing medium.

With regular media changes, cells cultured in HS-containing medium could be maintained without splitting and replating for at least 2 months.

Example 2: Culturing of Huh7.5 Cells in Hs Promotes Differentiation to a Primary Hepatocyte-Like Phenotype To further evaluate the effect of culturing cells in HS-containing medium, and to assess whether these cells underwent differentiation to a primary hepatocyte-like cell, level of expression of hepatocyte differentiation marker were assayed at 7 days and 21 days after transfer of Huh7.5 cells into HS-supplemented medium. After 7 days only minor changes in hepatocyte markers were observed. (FIG. 3A) However, after 21 days, the expression of the hepatic differentiation markers albumin and alpha1-antiTrypsin was increased approximately 4 fold in cells grown in human serum compared to FBS. The level of expression of these proteins is similar to the level of expression of human primary hepatocytes in culture. Culturing the Huh7.5 cells in primary hepatocyte medium (PHM) did not have a significant additional effect on the expression of albumin or alpha1-antitrypsin. Changes in LDL-receptor (LDL-R) were not significant in cells grown in HS, however, when Huh7.5 cells were grown in primary hepatocyte medium (PHM), LDL-R expression was increased.

Figure 3A:
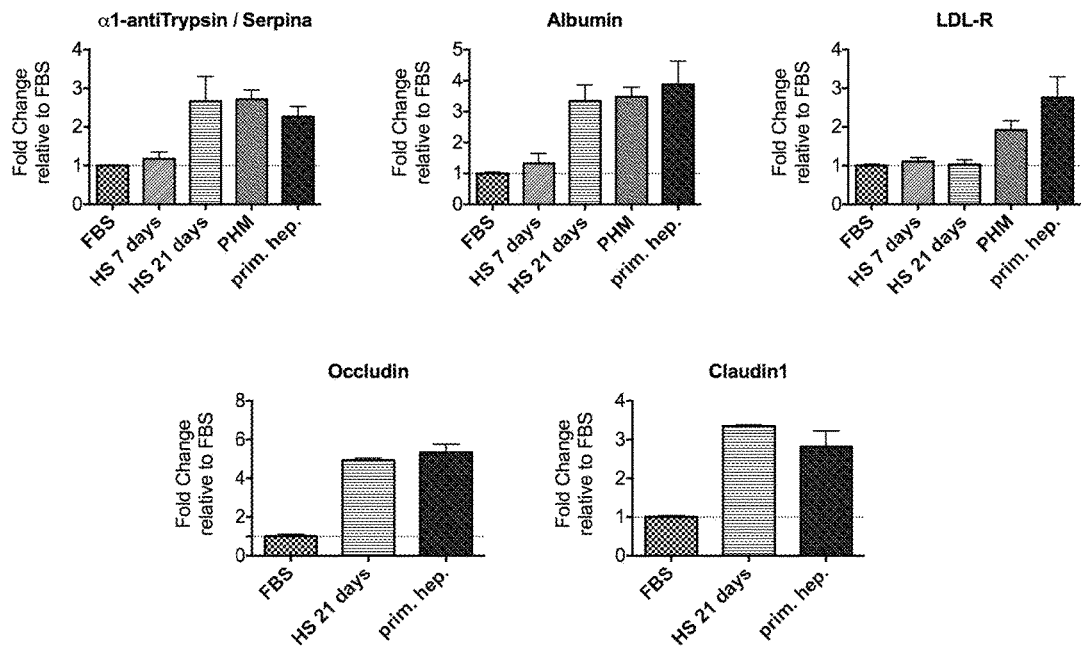
FIG. 3A is a set of graphs showing expression of the hepatocyte differentiation markers LDL-receptor, Albumin, and Alpha1-antiTrypsin, in cells maintained in FBS or in HS for 7 or 21 days, as well as HuH7.5 cells that were maintained in primary hepatocyte medium (PHM) and human primary hepatocytes in culture (prim. hep.) Also included is the expression of claudin-1 and occludin, two tight junction proteins that are highly expressed in liver

Expression of claudin-1 and occludin, tight junction components, was also increased in cells grown in human serum after 21 days, and comparable to expression in human primary hepatocytes in culture (FIG. 3A). High levels of tight junctions are present in liver tissue. Additionally, through immobilization of cells, these proteins are also known as potent tumor suppressors, and indicate the transition of a tumorigenic state to a more differentiated state of cells. Claudin-1 and occludin also function as entry receptors for HCV.

Figure 3B:
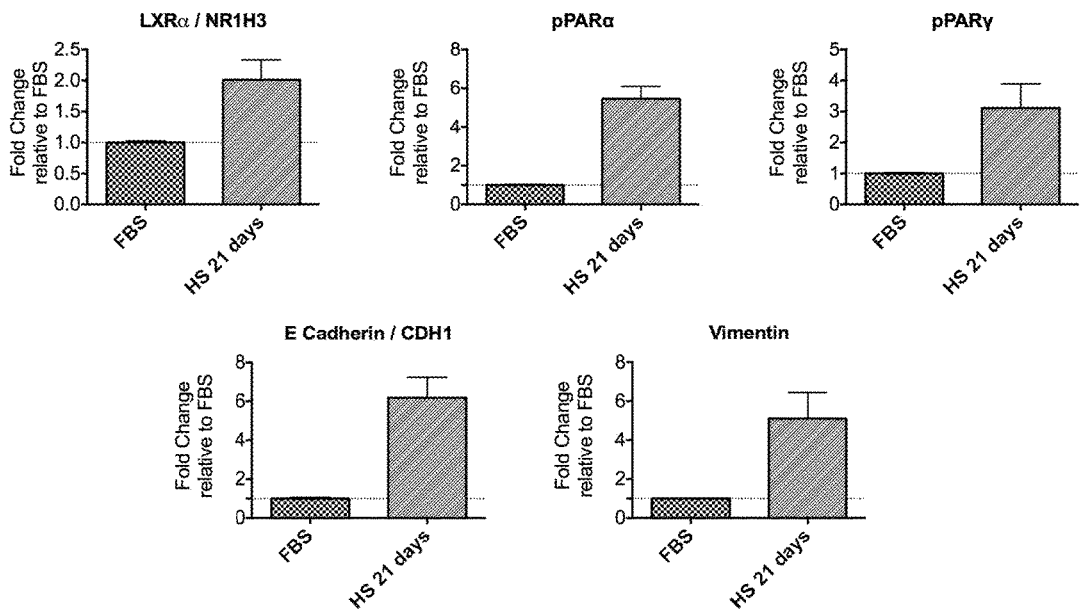
FIG. 3B is a set of graphs showing that key lipid metabolism regulators (Liver X receptor alpha (LXRα), Peroxisome Proliferator-Activated Receptor alpha and gamma (PPARα, PPARγ), are all highly expressed in cells that are cultured in HS. Cytoskeleton proteins vimentin and E-Cadherin are also increased in cells grown in human serum.

Expression of key lipid metabolism regulators was increased in cells that were grown in HS, compared to cells grown in FBS (FIG. 3B). LXRα (Liver X Receptor alpha) is highly expressed in liver, and controls transcriptional programs involved in lipid homeostasis and inflammation.

Peroxisome proliferator-activated receptors (PPARs) are key regulators of differentiation and metabolism. PPARα is a major regulator of lipid metabolism in the liver. Activation of PPARα promotes uptake and utilization of fatty acids by upregulation of genes involved in fatty acid transport and fatty acid oxidation. PPARγ regulates fatty acid uptake and storage as well as glucose metabolism. Cytoskeleton proteins vimentin and e-cadherin are also increased in cells cultured in human serum. Vimentin, is essential for maintaining shape and keeping organelles in place, it also controls the transport of low density lipoprotein inside the cell. E-Cadherin play an important role in cell to cell adhesion, and is therefore, like tight junction proteins, indicative of a non-proliferative/non-tumorigenic state of the cell.

Example 3: Examination of Other Culture Conditions

In order to compare the effects of culturing of HuH-7 or HuH-7-derived cells in human serum, other culture conditions were examined.

DMSO, (dimethyl sulfoxide) has been reported to induce growth arrest in HuH-7 or -derived cells, and other hepatoma cells. (Sainz et al. (2006) J Virol 80: 10253-10257). In order to assess the effect of DMSO, the level of expression of hepatocyte-specific genes in Huh7.5 cells grown for 3 weeks in the presence of 1% or 2% DMSO in DMEM (DMEM, 10% FBS, 1% or 2% DMSO, penicillin/streptomycin) was examined. Additionally, Huh7.5 cells were cultured in 2-10% adult bovine serum (ABS, Invitrogen) in DMEM in lieu of fetal bovine serum (DMEM, 2% ABS, penicillin/streptomycin.

Both culture conditions resulted in growth arrest, within approximately 7 days. Cells cultured in medium containing DMSO or ABS did undergo some morphological changes, but never to the extent of cells cultured in human serum. In either culture, a punctuate pattern in the cytoplasm indicative of a primary human hepatocyte phenotype was not typically observed (data not shown).

Figure 4:
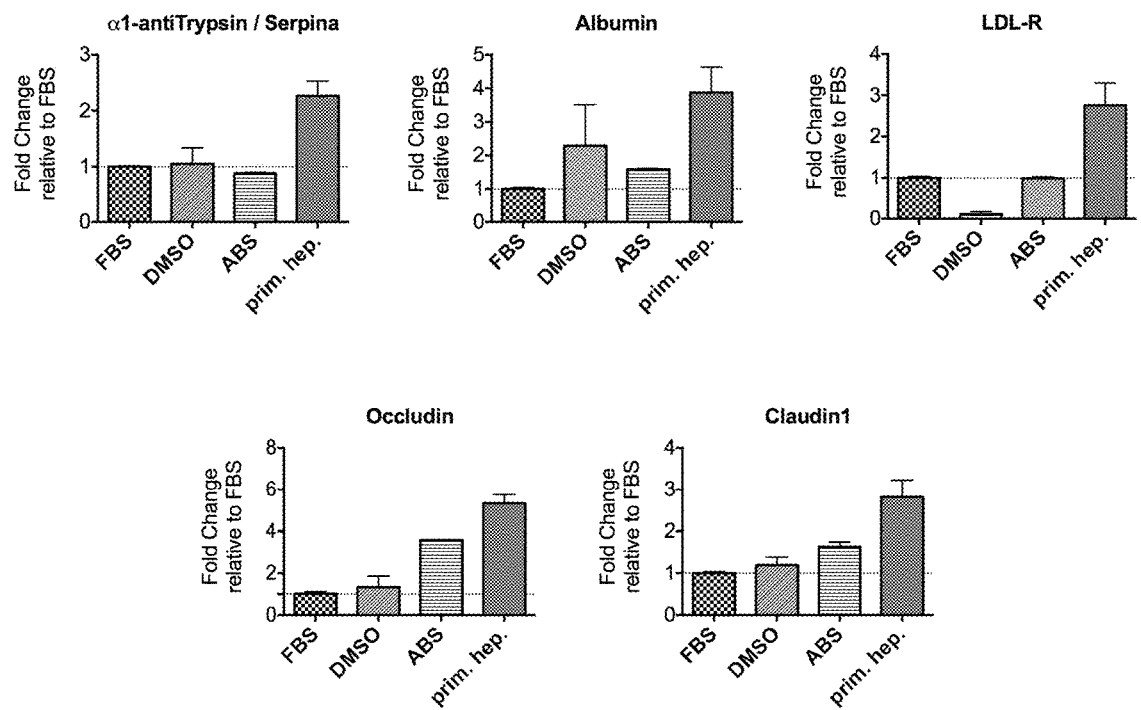
FIG. 4 is a graph showing the effect on above mentioned differentiation markers on cells grown in the presence of 2% DMSO, or 2% adult bovine serum (ABS), compared to FBS and cultured primary hepatocytes (prim. hep.). ABS and DMSO both induce contact inhibition/growth arrest, but do not induce increased expression of differentiation markers

The differentiation status of cells cultured in ABS or DMSO was examined by assessing the level of expression of the same hepatocyte differentiation markers as described in above (FIG. 4). Whereas culturing in 2% DMSO resulted in a slight increase in Albumin expression, and ABS resulted in a minor increase in expression of tight junction proteins claudin-1 and occludin, none of the proteins were expressed at a level comparable to those in primary human hepatocytes in culture or at a level comparable to expression in Huh7.5 cells cultured in human serum. The level of expression of other biomarkers tested was not significantly increased relative to culturing in medium containing FBS.

Figure 5A:
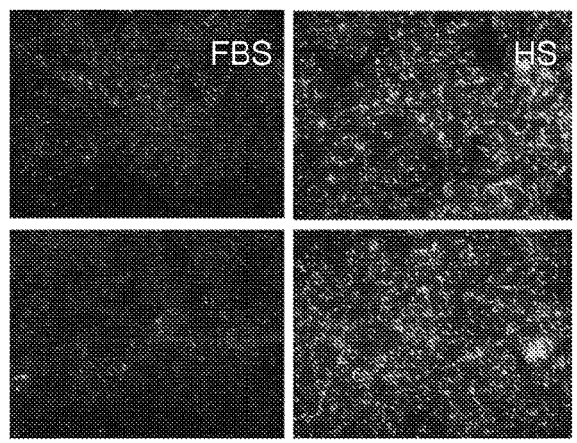
FIG. 5A is a set of photographs illustrating that cellular lipid droplets are increased in cells cultured in HS (right panels) as compared to FBS.
Figure 5B:
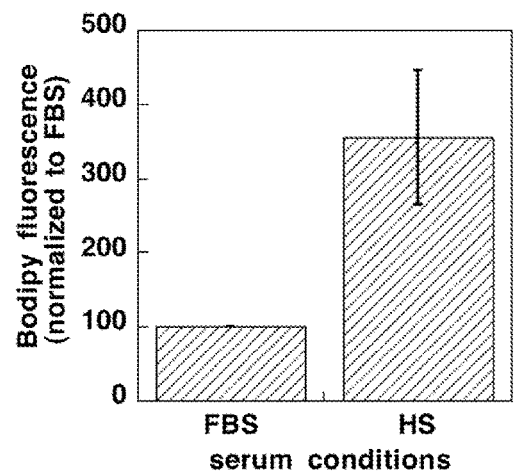
FIG. 5B is a graph showing quantitation of Bodipy fluorescence of cells maintained in FBS or HS (n>4).

Example 4: Effect of Culture Medium on Appearance of Cellular Lipid Droplets The appearance of cellular lipid droplets following culturing of Huh7.5 cells in FBS versus HS was examined. As shown in FIGS. 5A and 5B, Bodipy fluorescence indicative of lipids was much more intense in cells that are cultured in HS, compared to FBS. When quantitated using ImageJ software, Bodipy fluorescence intensity was approximately 4 times higher in cell cultures in HS than in cells cultured in FBS (FIG. 5B).

Additionally, the distribution of lipid droplets is affected by the different culturing conditions. In FBS medium, lipid droplet size in cells is heterogeneous. In HS medium, lipid droplets in cells are generally smaller than in FBS-cultured cells, and are much more uniform in size.

Example 5: Production of Viral Titers of JFH-1

JFH-1 was electroporated into FBS-cultured cells. The electroporated cells were then maintained in FBS or transferred to HS-containing media, immediately after electroporation, according to Example 1. At 4-6 days after electroporation, virus was harvested by collection of culture supernatants.

Virus produced by electroporation of cells maintained in FBS media is referred to as "JFH-FBS"; virus produced by electroporation of cells which were transferred to and maintained in HS medium immediately after electroporation, is referred to as "JFH-HS".

Figure 6A:
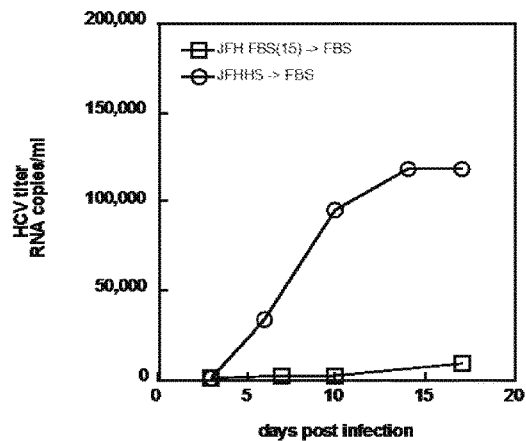
FIGS. 6A-6E are a set of graphs showing the results of infection of cells with the HCV strain JFH-1 ("JFH") where the cells are cultured in FBS or HS.

FIG. 6A shows infection of cells cultured in FBS with the two different viruses. When FBS maintained cells were infected with JFH-FBS that was isolated 4 days after electroporation (like JFH-HS), infection was not detected in these cells, because the RNA titers of these viral stocks were too low. In contrast, JFH-HS immediately resulted in high viral titers in FBS grown cells. Viral titers quickly reached a plateau. For comparison, JFH-FBS that was isolated 15 days after electroporation was used (referred to as JFH-FBS (15).) Viral titers of JFH-FBS(15) remained low throughout the infection course compared to JFH-HS.

Figure 6B:
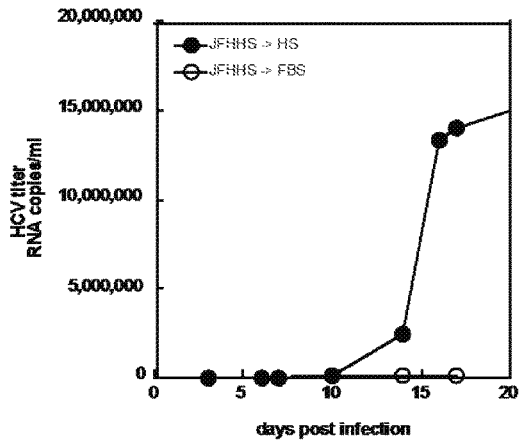

FIG. 6B shows viral titers of cells that were grown under the different conditions (FBS and HS), but that were infected with the same virus (JFH-HS). Notably, during the first 10 to 11 days of culture in HS, the benefit of using HS for viral production was not apparent. However, after about 11 days viral titers began to increase such that at about 14 days post transfer of cells to HS media, viral production rapidly increased in HS maintained cells. This increase in viral production was not observed in FBS-cultured cells. This timing corresponds to the approximate time at which HS-cultured cells exhibited a phenotype differentiated toward a phenotype resembling that of a primary human hepatocyte. Similar infections were performed in HuH-7 cells. Trends observed in HuH-7 cells (the fold increase was similar) were similar to those observed in Huh7.5 cells.

Figure 6C:
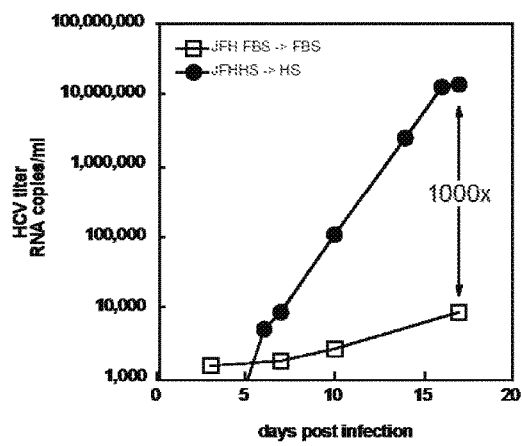
Figure 6D:
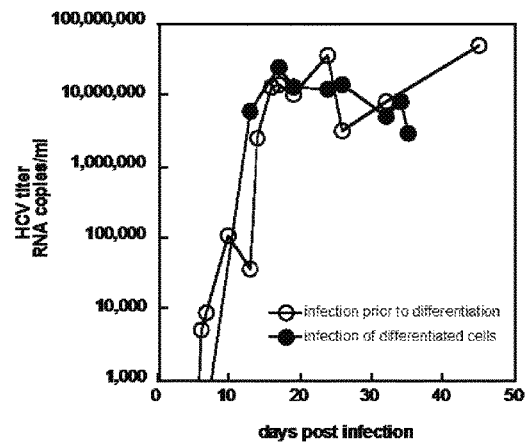

FIG. 6C shows that when cells grown in HS are infected with JFH-HS, viral production (HCV RNA copies per ml) increases about 1,000 fold, compared to the standard tissue culture conditions using JFH-FBS in FBS-cultured cells. Culturing of cells in HS-containing media allowed production of continuous viral titers approaching $10^8$ RNA copies/ml or more for at least 45 days, with changes to fresh HS-containing media every 3-4 days (FIG. 6D). When cells were first differentiated to the primary hepatocyte-like phenotype (by culturing in HS-containing media for about 14 days), and then infected with JFH-HS, similar viral titers were accomplished (FIG. 6C).

Figure 6E:
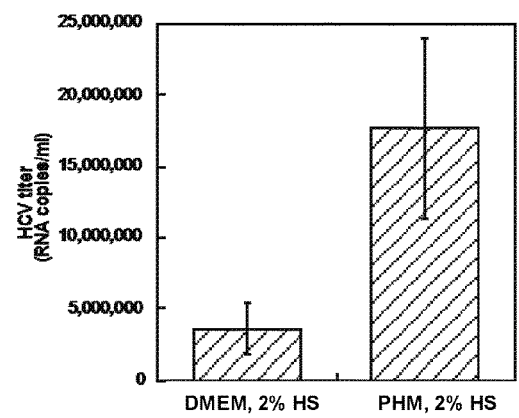

FIG. 6E show the effect of using primary hepatocyte medium on viral titers. Cells that were infected, and first differentiated using HS, were transferred to primary hepatocyte medium (DMEM, 1.2 µg/ml insulin, 11 µM hydrocortisone hemisuccinate, 15 mM Hepes, pen/strep, 200 mmol glucose, 2% human serum) and the effect on viral production was assessed. Within 3 day after transfer, the morphological changes seen as a result of culturing in HS became more distinct (not shown). Additionally, viral titers increased approximately 5 fold compared to the same cells that were maintained in DMEM/2% HS/pen/strep.

Example 6: Infection of Mice with JFH-HS and JFH-FBS

In vivo infectivity of both JFH-HS and JFH-FBS were tested in the chimeric SCID/Alb-uPA mouse model. JFH-HS stocks collected after electroporation were used to infect new cells, and the supernatant from these infected cells used to infect mice. Direct comparison to the same virus produced in FBS was not possible, since viral titers were too low to expect detectable infection. Therefore, a tissue culture adapted JFH variant (HCVcc) was used at a similar titer solely for purposes of comparison.

HCVcc, JFH viral stocks were produced by electroporation of cells cultures in FBS. Pooled virus was isolated every 5 days, from day 15 till day 30 post-infection. This pooled virus was used to infect cells grown in FBS. Subsequently, the supernatant of infected cells was used to infect fresh cells. This procedure was repeated for several rounds of infection. The resulting virus is thus tissue-culture adapted. Serum from an HCV-infected patient served as a positive control.

Figure 7:
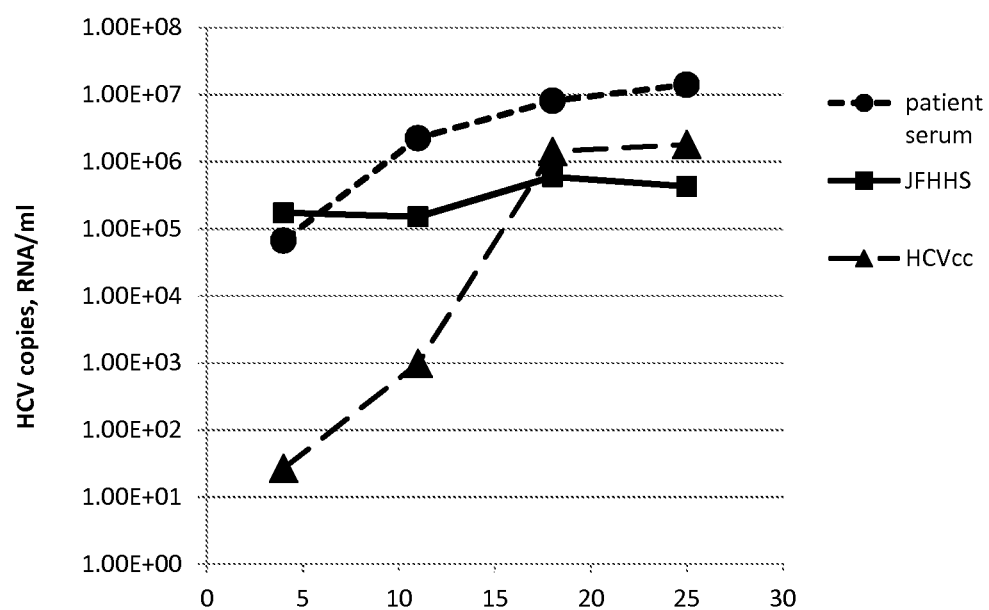
FIG. 7 is a graph showing the results of infection of a chimeric SCID/Alb-uPA mouse model with HCV-infected patient serum (circles), JFH virus produced by electroporation of HuH7.5 cells followed culture in HS-containing medium (JFH-HS, squares), or the tissue-cultured virus HCVcc (triangles)

FIG. 7 shows viral titers in mouse serum for up to 25 days post infection. JFHHS caused rapid infection of chimeric mice. JFHHS titers were detectable 4 days post infection at high titers, and only marginally increased further over the next 3 weeks. In contrast, viral titers of a tissue culture adapted JFHFBS slowly increased over the first 2 weeks and then appeared to reach the same plateau. Similar to JFHHS, viral titers of a highly infectious patient serum HCV also are detectable within 4 days.

Example 7: Effect of HS-Cultured Cells Upon HCV Particle: Viral Density, Lipoprotein Association In order to assess whether the biophysical properties of the virus were affected by culturing in HS versus FBS, viral density and ApoB association of the virus was assessed.

Figure 8:
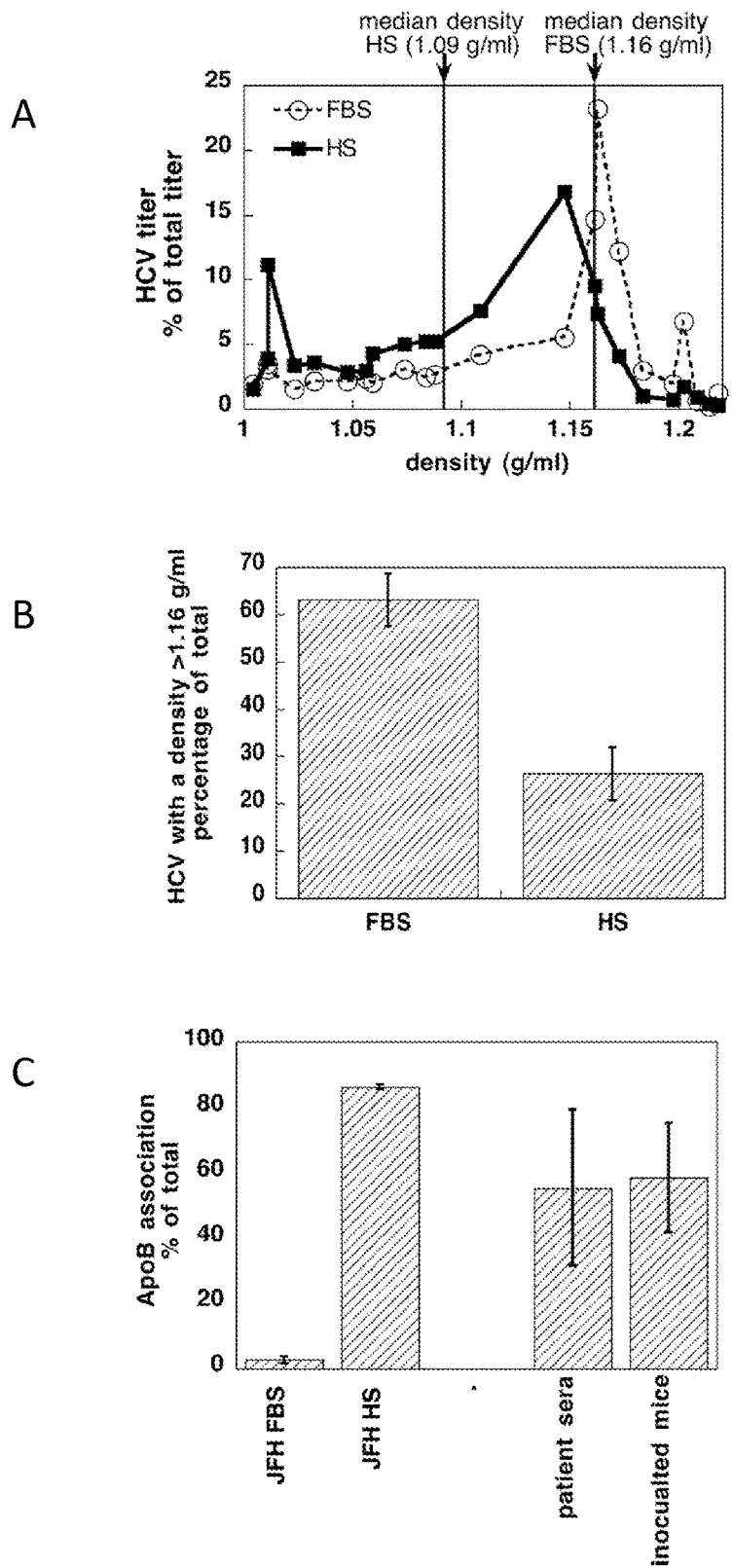
FIG. 8 is a set of graphs showing the effects of human-serum containing cultures on HCV. Panel A: Viral density of viruses produced from cells cultured in FBS (circles) or human serum (squares) as determined by sucrose gradient centrifugation; Panel B: Quantitation of viral density distribution of viruses produced from cells cultured in FBS or human serum (HS); and Panel C: Apolipoprotein B association of different viral variants. JFH FBS: JFH-1 produced from cells cultured in FBS; JFH HS: JFH-1 produced from cells cultured in HS; patient sera.

As shown in FIG. 8, Panel A the density of the virus cultured in HS shifts towards a lower density. Under standard tissue culture conditions using FBS, the median density of JFH was 1.16 g/ml, which is well in line with previous reports. Upon culturing cells in HS, the overall density of the viral particles shifts towards a lower density, with a median density of 1.09 g/ml, and the additional appearance of a very low density peak. Viral density was both determined in produced by HuH-7 and Huh7.5 cells, and results were similar in both cell types.

An alternative representation is shown in FIG. 8, Panel B. When produced in FBS-cultured cells, about 75% of the virus had a density higher than 1.16 g/ml, whereas when produced in HS-cultured cells, only about 25% of the virus has a density of >1.16 g/ml.

It has been previously reported that virus produced in tissue culture is not associated with ApoB, but is associated with ApoE. In human serum, and in the HCV infection mouse model, a significant portion of HCV is associated with ApoB (about 60%). Thus the effect of altered tissue culture conditions on HCV association with ApoB was examined.

Under standard tissue culture conditions using FBS, only approximately 5% of JFH was associated with ApoB. When cells were cultured in human serum, approximately 90% of the virus was ApoB associated (FIG. 8, Panel C). For comparison, in patient sera about 30-80% of HCV has been observed to be associated with ApoB, and about 40-70% of HCV in chimeric mouse sera has been observed to be associated with ApoB. ApoB association was determined in virus produced by HuH-7 and Huh7.5 cells, and results were similar.

Example 8: Effect of Human Low Density Lipoprotein (hLDL) on Viral Production in HS-Cultured Cells To examine the effect of lipoproteins on viral production, human serum deficient in Apolipoprotein B containing lipoproteins (VLDL and LDL) was prepared. Low (LDL) lipoprotein- and very low density (VLDL) lipoprotein-depleted HS was prepared by running the serum over a heparin column according to the instructions provided by the manufacturer (HiTRAP Heparin HP, GE Healthcare). Heparin binds ApoB containing lipoproteins, VLDL and LDL, at a high affinity, whereas HDL does not bind heparin. The resulting serum is therefore depleted of VLDL and LDL only. In short, after equilibration with binding buffer, serum was applied to the column, allowing the ApoB containing lipoproteins to bind. ApoB depleted fractions were collected and filter sterilized and stored at $-20°$ C.

Figure 9:
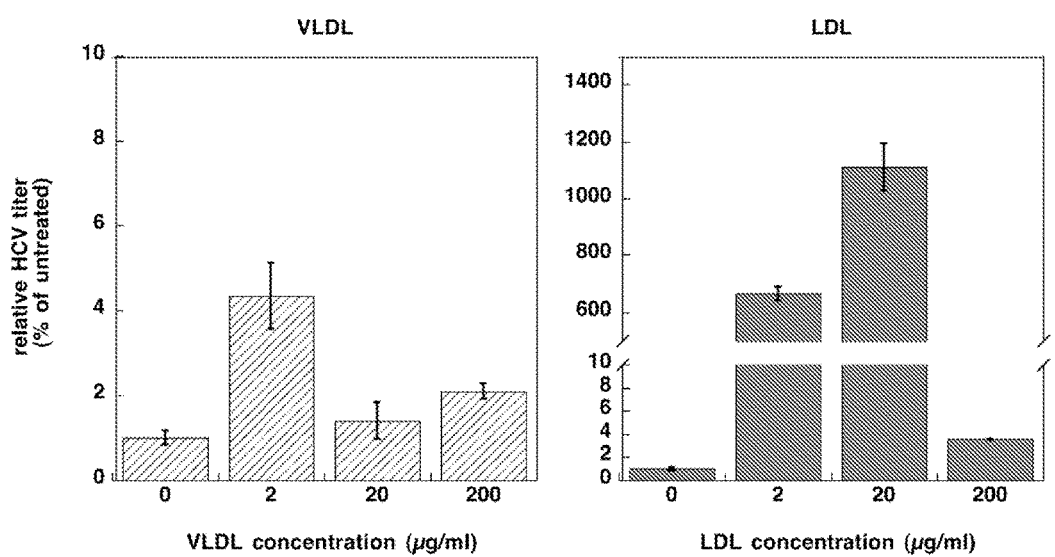
FIG. 9 is a set of graphs showing the effect of addition of ApoB-containing lipoproteins to differentiated cells. Left panel: Effect of addition of human VLDL to differentiated cells on viral production; Right panel: Effect of addition of human LDL to differentiated cells on viral production.

When cells were cultured in lipoprotein-depleted HS, much of the beneficial effect of human serum on production of high viral titers was lost, although differentiation of the Huh7.5 cells into the primary hepatocyte-like phenotype still occurred. Adding back human VLDL did not rescue the viral production. However, addition of human LDL did result in a 1000-fold increase in viral production. This effect of human LDL was dose dependent, and only can be achieved in cells that are (partially) differentiated (FIG. 9).

Example 9: Infection of Cells with Serum from HCV Infected Patients

Figure 10:
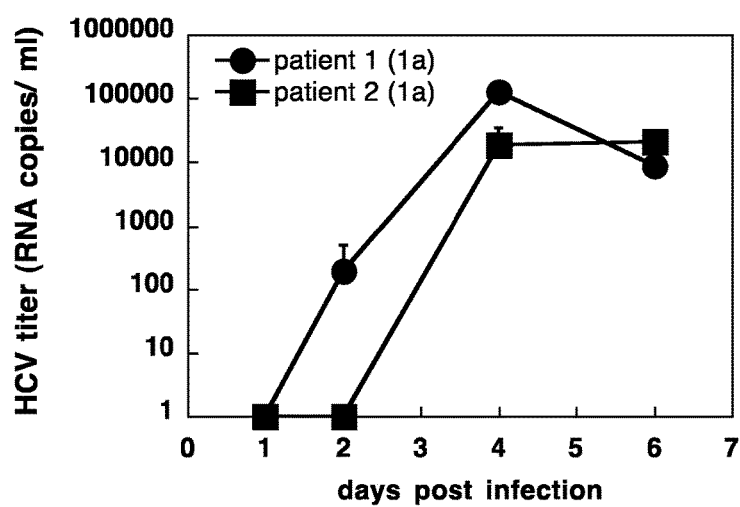
FIG. 10 is a graph showing infection of cells maintained in human serum with HCV positive serum from 2 different patients (patient 1: circles, patient 2: squares, both genotype 1A).

Huh7.5 cells cultured in human serum were tested for susceptibility to infection by serum from HCV patients infected with HCV genotype 1a. Successful infection was achieved with viral titers of up to about $10^5$ RNA copies/ml. (FIG. 10) In contrast, Huh7.5 cells cultured in FBS-containing medium and infected with the same serum did not produce detectable virus as assayed by RT-PCR.

The Examples above illustrate that culturing of hHCC cells, such as HuH-7-derived cells, in human serum results in the differentiation to a phenotype of a primary hepatocyte. HuH-7 or Huh7.5 cells cultured in medium containing human serum (rather than FBS according to conventional tissue culture protocols) become contact inhibited and show an increase in expression of several hepatocyte differentiation markers, including claudin-1 and occludin, two factors that have been implicated as entry receptors for HCV. Additionally, HS-cultured cells show an increase in cellular lipid droplets, the organelle that has been implicated as the site of HCV replication and/or assembly.

Infection of HS-cultured hHCC cells with HCV shows a 1,000 fold increase in viral production compared to the standard tissue culturing methods using DMEM supplemented with FBS. Shortly after FBS-containing medium of hHCC cell cultures is replaced with HS-containing medium, an increase in viral titers of about 10-100 fold is observed. Around the time differentiation of HS-cultured hHCC cells to a primary hepatocyte phenotype is achieved (around 14 days), viral replication is increased about 1,000-fold compared as to compared to hHCC cells maintained in FBS-containing medium. Results are shown in FIG. 9.

Human LDL plays a role in the increase of viral titers. Removal of VLDL and LDL from the serum prevented the increase in viral titers associated with HS-culture conditions. Selective addition of human LDL, but not human VLDL rescued the viral production levels of HS-culture conditions. The differentiation state of the hHCC cells played a role in the beneficial effect of LDL on viral titers.

HCV particles produced from HS-cultured hHCC cells differ structurally from HCV produced from FBS-cultured hHCC cells. HCV particles produced from HS-cultured hHCC cells have a lower density and are ApoB associated. Lower density of HCV fractions has been linked to higher infectivity. Higher infectivity was indeed observed in the chimeric mouse model. Virus produced from HS-cultured cells exhibited a similar infection time course as a HCV from highly infectious patient serum, indicative of higher infectivity as compared to virus produced from FBS-cultured hHCC cells. The lower density and ApoB association of HCV produced in HS-cultured hHCC cells more closely resembles virus circulating in the blood stream of patients.

HS-cultured cells can be used to produce higher titers of virus as compared to the same virus produced in FBS-cultured cells. As shown above, JFH-1 was produced from HS-cultured cells at much greater titers than in FBS-cultured cells without the need for genetic modification of the virus and/or prior tissue culture-adaptation to select adaptive mutations. HS cultured cells transfected with JFH-1 and cultured for 13 days produced virus particles which were infectious for HS cultured cells and the virus produced by these cells was highly infectious in chimeric mice.

Example 10: Lipoprotein Secretion in HS-Cultured Cells

Hepatocyte-specific functions, such as VLDL secretion, is absent in hHCC grown in FBS supplemented serum. VLDL secretion occurs in hHCC cultured in human serum, Huh7.5 cells cultured in FBS supplement serum were switched to media supplemented in human serum (HS) as described in Example 1 and triacylglyceride (FIG. 11) and cholesterol (FIG. 12) based lipoprotein profiles were obtained from the media of the cultured cells at various time points, using size exclusion fast-protein liquid chromatography.

In line with previous observations (Ling et al. (2013) Biochim Biophys Acta 1831(2): 387-97; and Meex et al. (2011) J Lipid Res 52:152-158), VLDL secretion was absent in Huh7.5 cells that were grown in FBS supplemented serum (FIG. 11, Panel B and FIG. 12), and only a small LDL-sized peak was observed. After 5 days of culturing in human serum, there was a small increase in VLDL secretion, and minor changes were observed in the LDL and HDL sized fractions on cholesterol profiles (FIG. 12).

Figure 11:
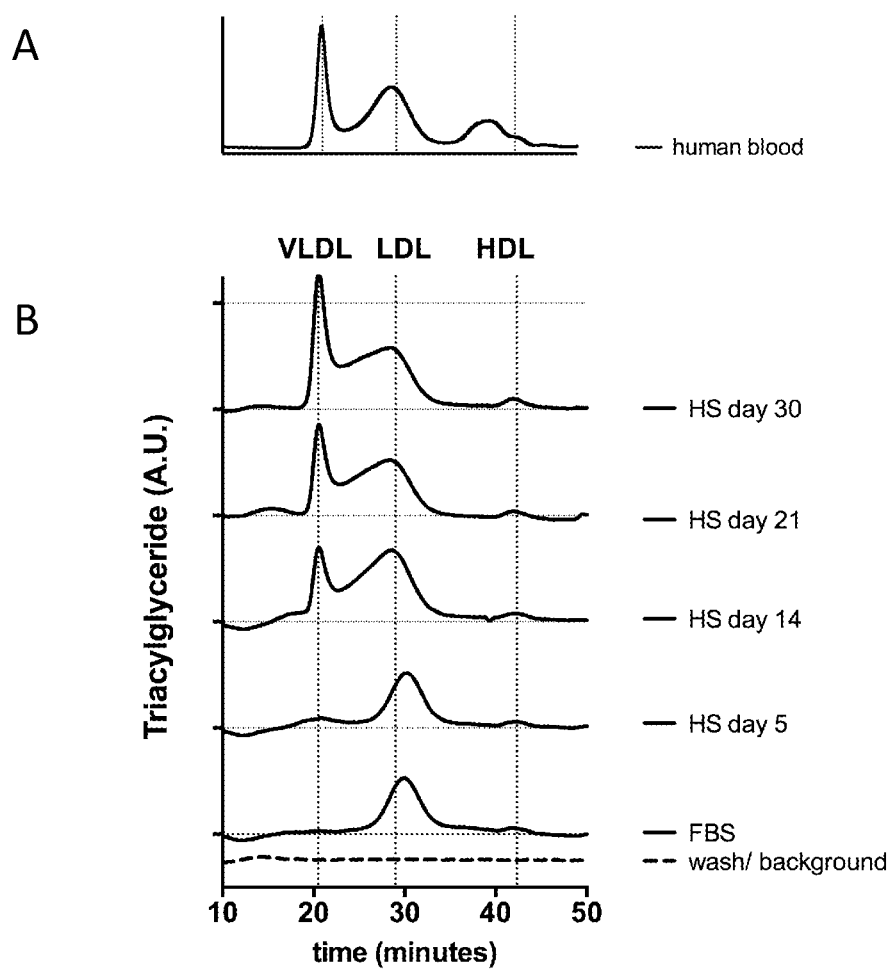
FIG. 11, Panels A and B are graphs showing triacylglyceride-based lipoprotein profiles of human blood (A) and media from Huh7.5 cells cultured in human serum (HS) for various lengths of time (B). Lipoprotein separation was performed using size exclusion fast-protein liquid chromatograph (FPLC).
Figure 12:
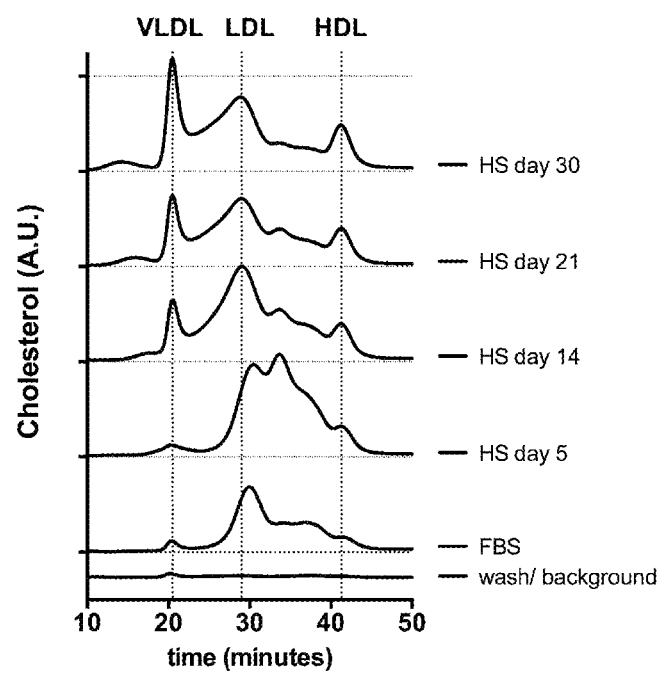
FIG. 12 is a graph showing a cholesterol-based lipoprotein profile of media taken from Huh7.5 cells cultured in human serum (HS) for various lengths of time. Lipoprotein separation was performed using size exclusion fast-protein liquid chromatograph (FPLC).

VLDL secretion, however, was present in cells cultured in human serum upon cell differentiation (from 14 days on), as indicated by the prominent VLDL peaks shown in the lipoprotein profiles (FIG. 11, Panel B and FIG. 12). Additionally, upon differentiation of the cells, the LDL peaks both increased in size (area under the curve is larger) and larger LDL particles were present (LDL peaks shifted left (larger particles elute first)). On day 30 of culturing in HS, the lipoprotein profile of the media from the HS cultured cells closely resembled the lipoproteins secreted by primary human hepatocytes in culture (Ling et al. (2013) Biochim Biophys Acta 1831(2): 387-97) and the lipoprotein profile of human blood serum (FIG. 11, Panel A, Steenbergen et al. (2010) 299:G844-854). An increase in the HDL peak was also observed in the cholesterol based lipoprotein profiles (FIG. 12). Taken altogether, this data shows that lipoprotein secretion can be restored in HS cultured cells secrete lipoproteins and exhibit a secreted lipoprotein profile similar to that found in human serum and produced by primary human hepatocytes.

Example 11: Infection of Cells with HBV

The susceptibility of hHCC cells to infection with Hepatitis B virus (HBV) was examined. The expression level of a putative HBV entry receptor, the sodium taurocholate cotransporting polypeptide (NTCP, SLC10A1), was also monitored.

Huh7.5 cells were cultured as described above in human serum (HS) containing media for 21 days to produce differentiated cells. Following this period, the cells were infected with HBV for 24 hours or 48 hours. Infection was accomplished by either adding 50-100 µl of HBV positive serum from an infected patient to the cell culture, at an multiplicity of infection (MOI) of 15-30 viruses per cell (or higher), or by adding 10 µl of a 50× concentrated sample of cell supernatant from cultured HepAD38 cells, a cell line that is genetically modified to express HBV particles. For HepAD38 cells an MOI of approximately 1000 viruses per cell was used.

Cells were washed extensively following infection to remove unincorporated virus. Viral secretion into the media was monitored by determining the amount of viral genomes in the media, on different days post infection, using quantitative PCR.

Figure 13:
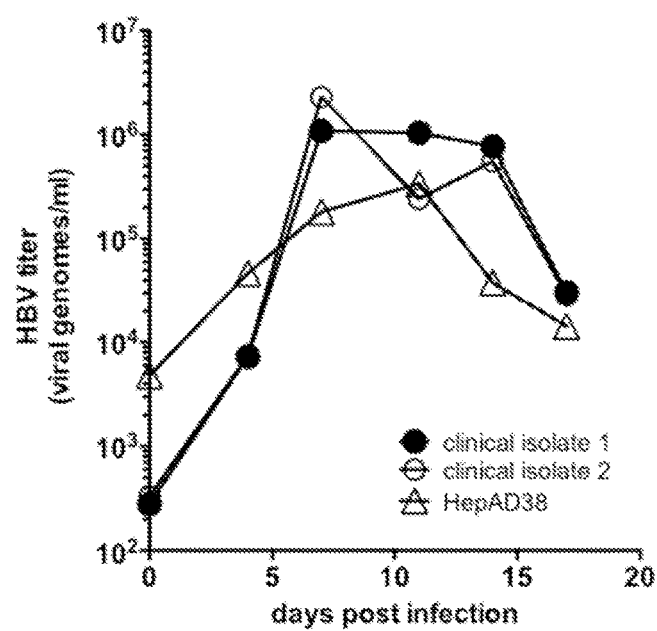
FIG. 13 is a graph showing HBV production following infection of Huh7.5 cells cultured in human serum (HS).

As shown in FIG. 13, HS-cultured cells were successfully infected with two different clinical isolates of HBV (open circles and closed circles), as well as with virus produced by HepAD38 cells (open triangles). After approximately 4 days post infection, viral titers were detected that exceeded the viral titers in the wash (where the wash was at either day 1 or day 2 post-infection (day 0)). Viral titers reached a maximum at approximately 5-14 days. After 15 days post-infection viral titers decreased, coinciding with decreasing entry receptor levels.

Example 12: Expression of an HBV Entry Receptor in HS-Cultured Cells

The sodium taurocholate cotransporting polypeptide (NTCP) has been reported to be an entry receptor for HBV in human cells (Yan et al. (2012) eLife 1:e00049). Expression of NTCP at the mRNA level was assess in Huh7.5 cells were cultured in HS as described above for different lengths of time (0-35 days). Huh7.5 cells cultured in FBS and isolated at the same passage number served as a control. At the end of each culturing period, cell lysates were prepared in TRIZOL® (Invitrogen) according to the instructions by the manufacturer. Relative mRNA levels of NTCP were determined compared to HPRT using quantitative PCR.

Figure 14:
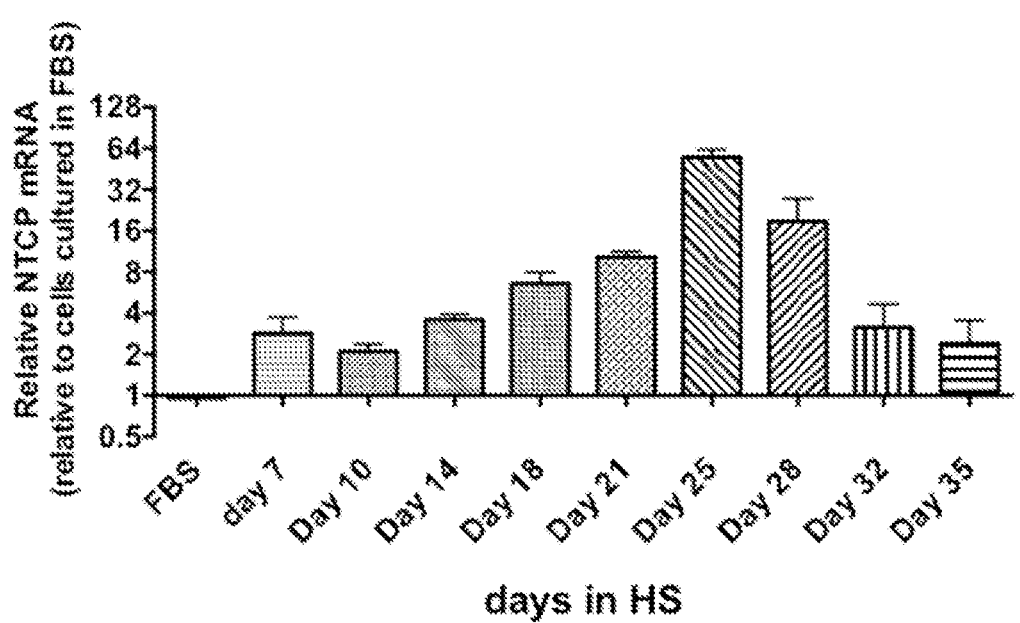
FIG. 14 is a graph showing NTCP expression in Huh7.5 cells cultured in FBS or in human serum for different time periods.

As shown in FIG. 14, HS-cultured cells exhibited increased levels of NTCP shortly after transfer to human serum-containing media. The highest level of expression of NTCP was observed 25 days after the transfer to HS, showing a 60-fold increase compared to FBS. At about day 28, NTCP levels began to decline.

Because NTCP is has a function as a bile exchanger, these data indicate that bile secretion, a liver specific function, is increased or restored in HS-cultured cells. In addition, in view of the NTCP expression levels, these data indicate that shorter differentiation times of hHCCs in HS-containing medium (e.g. 10-14 days) are sufficient to provide for HBV infection.

Example 13: Use of Heparin-Treated Serum in the Tissue Culture Media Enhances Infection and Increases Viral Titers Lipoproteins were removed from serum by eluting the serum over a Heparin column (according to the instructions of the manufacturer; HiTrap Heparin column, GE Healthcare). Heparin binds Apolipoprotein B (ApoB) with a high affinity. Serum (FBS or HS) was applied to the columns and the run-through was collected. The run-through fractions are essentially free of ApoB containing lipoproteins, such as LDL and VLDL.

Huh7.5 cells initially cultured in FBS were infected with the same amount of virus (HS produced virus, thus ApoB associated virus) and then further maintained in FBS, HS, Heparin-treated FBS (HepFBS) or Heparin-treated HS (HepHS) for up to 28 days. Cell viability was not affected by culturing in HepFBS or HepHS. Viral titers were monitored during the 28 days.

Figure 15:
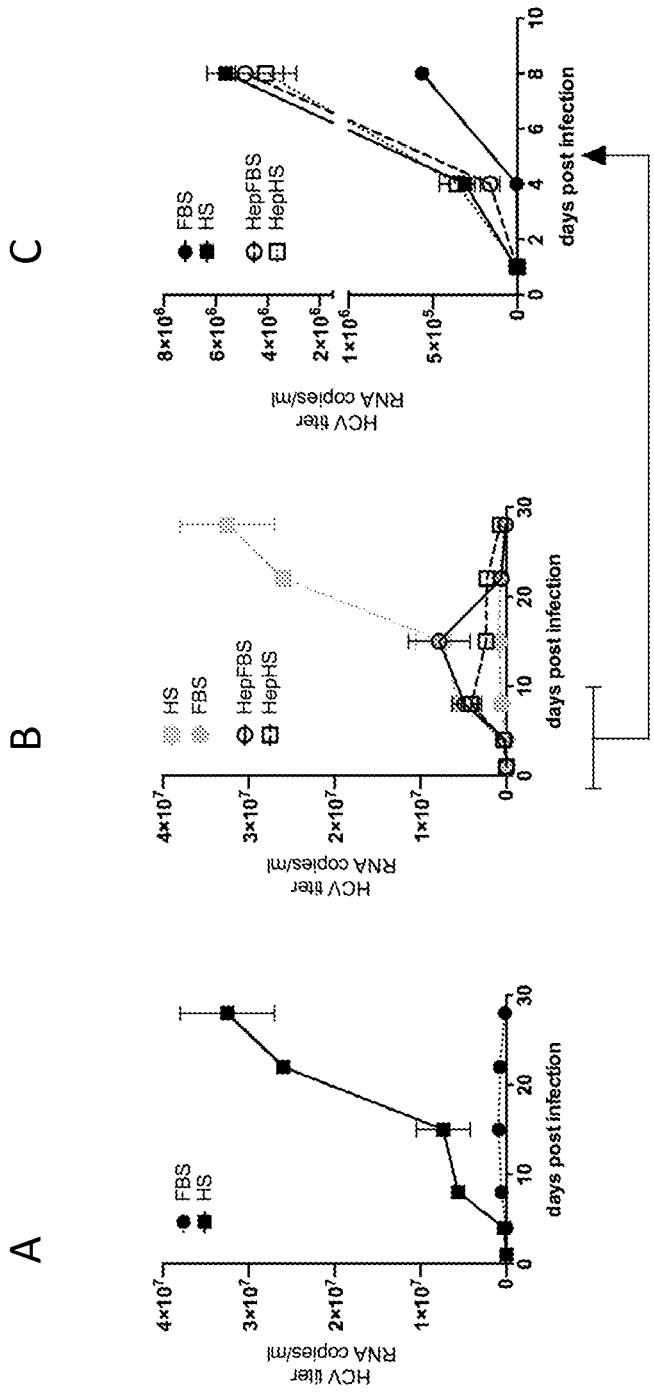
FIG. 15 is a set of graphs showing a comparison of HCV viral production in different culture media (FBS, HS, and heparin treated FBS and HS (HepHS and HepFBS). Panel A: Viral titers in cells cultured in HS (squares) or FBS (circles). Panel B: Viral titers in cells cultured in HepFBS or HepHS. Panel C: Enlargement of the first 8 days of Panel B.

FIG. 15, Panel A shows viral titers in cells cultured in HS or in FBS. As expected, viral titers in HS (squares) far exceeded viral titers in FBS (circles). FIG. 15, Panel B shows viral titers in cells cultured in HepFBS or HepHS. In the first 10-15 days viral titers in HepHS and HepFBS exceeded titers in FBS, However over time, HepHS, HepFBS and FBS resulted in similar titers. FIG. 15, Panel C is an enlargement of the first 8 days of Panel B, and it shows that HS, HepFBS and HepHS culturing results in titers that are similarly enhanced relative to cells cultured in FBS during this period.

These data indicate that enhanced viral titers relative to those achieved using untreated FBS can be achieved by culturing cells in using serum depleted of lipoproteins (e.g., by heparin treatment) at the time of viral infection. Surprisingly, enhanced viral titers can be achieved using either Heparin-treated human serum or Heparin-treated fetal bovine serum.

Example 14: Increasing Infection Rates of Purified, Lipoprotein Associated Virus (HS Produced Virus)

Figure 16:
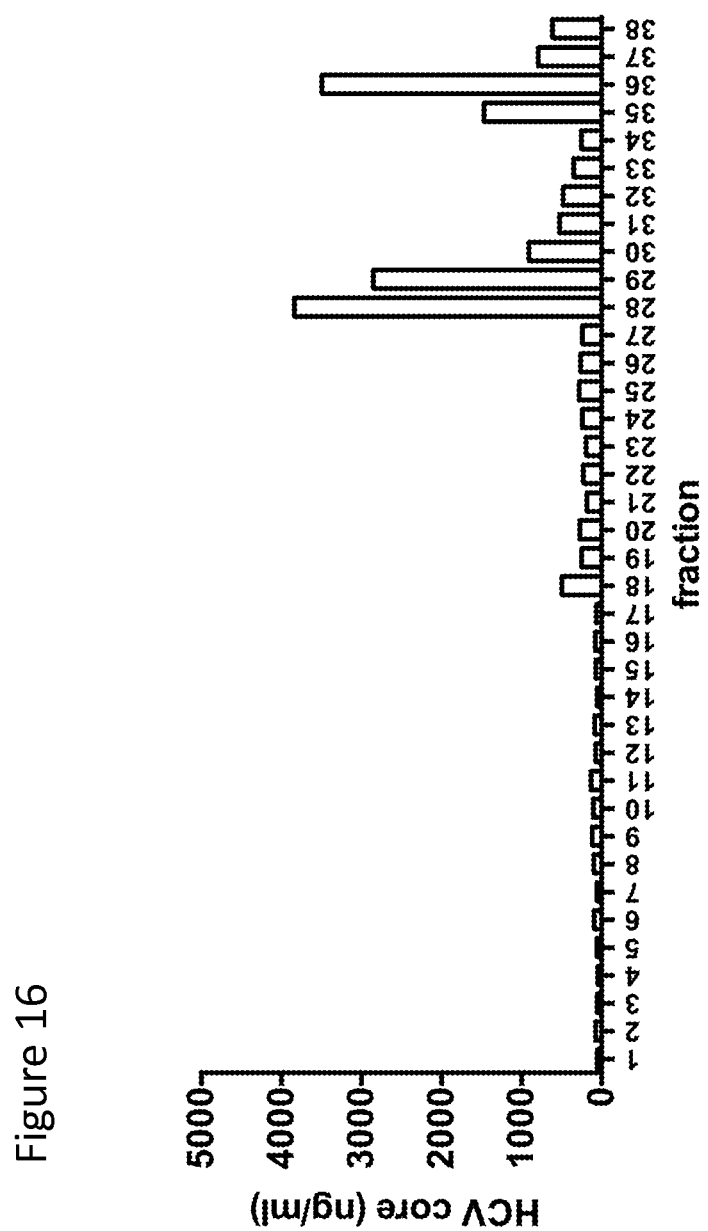
FIG. 16 is a graph showing purification of HCV using a heparin column. HCV was detected by quantitation of HCV core protein in each fraction.

Virus produced in human serum is associated with human Apolipoprotein B (ApoB). This property was exploited to purify virus from sera from an HCV-infected patient using the high binding affinity of ApoB to Heparin. Virus produced in HS-cultured cells was concentrated using a 300 kDa filter in a Centrimate 500S tangential flow apparatus to 60 ml. This was loaded onto HiTrap heparin columns (run through fractions 1-10 [no HCV present, as detected by viral core protein ELISA]). The column was washed with 120 ml of wash buffer (0.1M NaCl 20 mM NaPO4 buffer ph7.4-made by standard techniques) (fractions 11-17). The column was then eluted with 0.2 M NaCl, 20 mM NaPO4 buffer ph7.4 (fractions 18-27), with 0.4 M NaCl, 20 mM NaPO4 buffer ph7.4 (fractions 28-34) and finally with 1M NaCl, 20 mM NaPO4 buffer ph7.4 (fractions 35-38). HCV core protein was quantitated in each fraction using ELISA. As shown in FIG. 16, two peaks were present (pooled fractions 28-30, and 35-37).

The purified virus from each fraction was diluted 100 times, and the infectivity of the virus tested by 4 hours of infection of cells cultured in either FBS or in Heparin-depleted HS (HepHS). The same amount of purified virus was used for both conditions. Infection rates were determined by staining for HCV NS5a, 2 days post infection as described previously (Lindenbach et al, 2005 Science Vol. 309 pp. 623-626) Infected cells will develop to a dark brown color (dark grey in greyscale).

Figure 17:
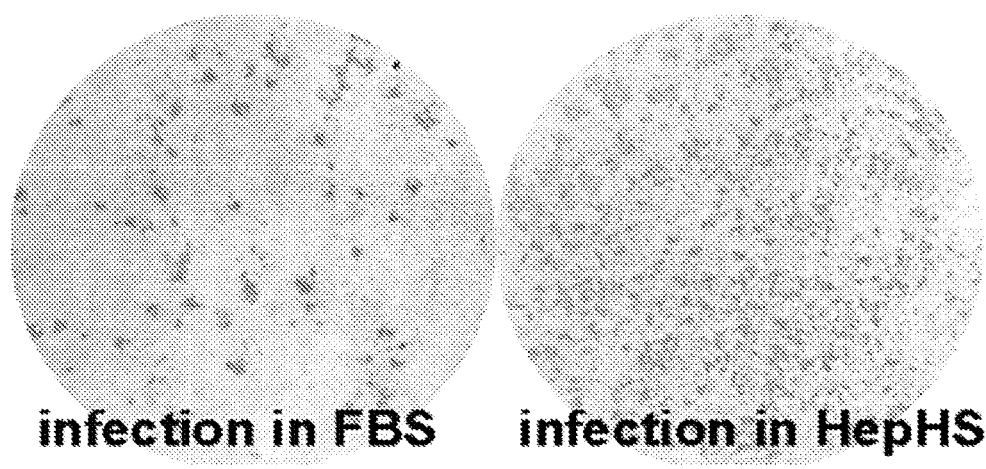
FIG. 17 is an image showing infection of cells cultured in FBS, or in HepHS for 2 days, with virus that was purified using a heparin column.

Fractions 35-37 were relatively poorly infectious (with infectivity similar to that of unpurified virus in FBS), and infection rates were not affected by removal of lipoproteins (not shown). Virus from fractions 28-30 successfully infected cells. As shown in the example provided in FIG. 17, much higher infection rates can be achieved in serum where the heparin-binding lipoproteins were depleted.

Example 15: Infection of Huh7.5 Cells with Clinical Isolates of HCV (Genotype 1a)

The susceptibility of HS-cultured Huh7.5 cells to infection by clinical isolates of HCV was tested. An infection protocol was developed to facilitate entry of lipoprotein associated-HCV, using cells that secrete lipoproteins could result in successful infection with clinical isolates of HCV.

In order to avoid the presence of human antibodies in serum obtained directly form patients, HCV clinical isolates were first passaged in SCID/Alb-uPA mice transplanted with human liver cells ("chimeric mice") (U.S. Pat. No. 6,509, 514; Mercer et al. (2001) Nat. Med. 7:927-33). Although humans can generate neutralizing antibodies, chimeric mice do not. Thus, the HCV positive serum from HCV-infected chimeric mice is free of HCV neutralizing antibodies.

Chimeric mice were infected with an HCV genotype 1a clinical isolate. Blood samples were harvested at different time points, and the amount of virus in the serum assessed by quantitative RT PCR. A HCV positive mouse serum sample (mouse A578) with a viral titer of $10^7$ RNA copies/ml was used to infect cultured cells.

Cells were cultured in human serum containing media for up to 10-21 days to differentiate cells. 2 days prior to infection cells were placed in HepHS as described above. Cells were then infected with HCV positive mouse sera, at 1 to 3 viral genomes per cell. Simultaneously cells cultured in media containing normal serum (HS) were infected with the same amount of virus. Cells were infected for 24 hours; thereafter the media was replaced with serum containing normal human serum (HS). Viral titers were monitored using quantitative RT PCR. The samples with the highest viral titers were then used to directly inoculate fresh cells, using the same cell infection protocol.

Figure 18:
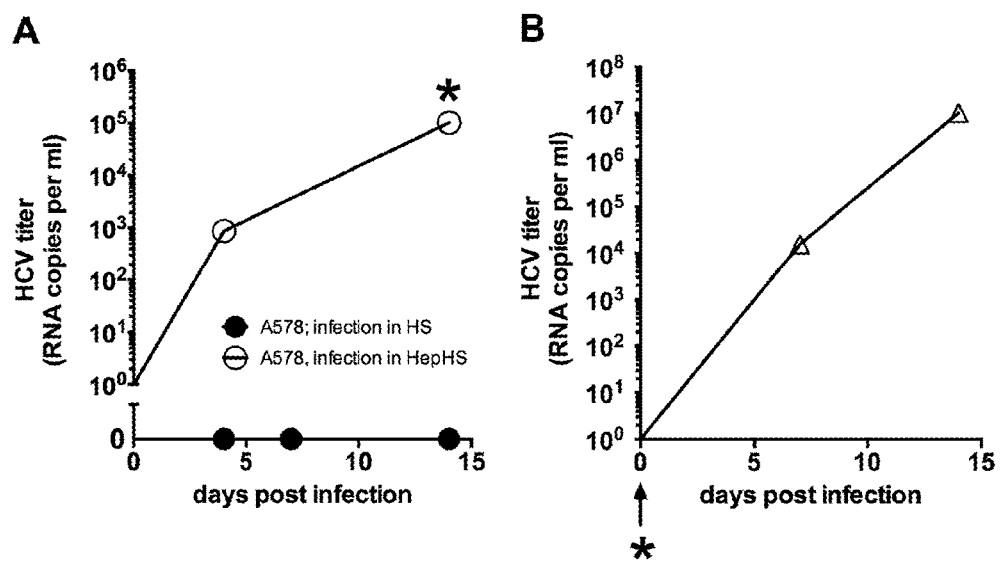
FIG. 18 provides graphs showing infection of HS-cultured Huh7.5 cells with mouse passaged HCV genotype 1a (Panel A) or with supernatant from cells at the timepoint indicated by the asterisk (*) in Panel A (Panel B). Cells in Panel B were differentiated in HS, placed in HepHS for 2 days, and then infected.

As shown in FIG. 18, cells that were cultured in normal human serum could not be detectably infected with HCV positive mouse serum A578 (closed circles, A578). However, when cells were cultured in lipoprotein-depleted serum during the infection stage, viral titers of up to $10^5$ RNA copies/ml were obtained (A578 HepHS; open circles). Day 15 samples (marked with an asterisk) from A578 HepHS were then used to infect new cells, using the same infection protocol. After 7 days viral titers were approximately $10^4$ RNA copies per ml, and after 14 days viral titers approached $10^7$ RNA copies per ml

Example 16: Analysis of Expression of Genes Involved in Drug Metabolism

As illustrated above, culturing human hepatocellular carcinoma (hHCC) cells (e.g., HuH-7 or Huh7.5 cells) in human serum (HS) containing media, instead of the standard fetal bovine serum (FBS) containing media, induces these cells to differentiate. As further shown above, culturing hHCC cells in human serum restores albumin and VLDL secretion, indicating these cells have become more hepatocyte-like. Here the differentiated cells were tested to assess whether these cells could serve as a model of primary human hepatocytes with respect to drug metabolism.

A genome wide microarray study comparing cells cultured for various times in HS containing media with cells grown in FBS containing media was conducted. Cells were cultured as before in HS containing media for 8, 15, or 23 days, and duplicate wells were harvested using Trizol (Invitrogen). Cells in FBS media were harvested at confluency. RNA was extracted according to the manufacturer's instructions, and cDNA synthesized using random primers and MMLV reverse transcriptase. Affymetrix Human PrimeView arrays were then performed and the data analyzed using the Robust Multi-Array Analysis method (RMA).

Drug metabolism is divided into three phases. In Phase I, enzymes such as cytochrome P450 oxidases introduce reactive or polar groups into xenobiotics (such as small molecule drugs). These modified compounds are then conjugated to polar compounds in P, which are catalyzed by transferase enzymes such as glutathione S-transferases. In Phase III, the conjugated xenobiotics may be further processed, before being recognized by efflux transporters and pumped out of cells. The present analysis was focused on Phase I and Phase II metabolism genes, and transporters predicted to be involved in drug metabolism in previous studies. (Jennen et al. (2010) Drug Discovery Today 15:851-858). The general families of genes were cytochromes (16 genes), alcohol dehydrogenases (8 genes), aldehyde dehydrogenases (18 genes), methyl transferases (8 genes), glutathione transferases (13 genes), Sulfotransferases (11 genes), UDP glucuronosyltransferases (11 genes), and ABC transporters (26 genes). The results are shown in FIGS. 19-22.

Figure 19:
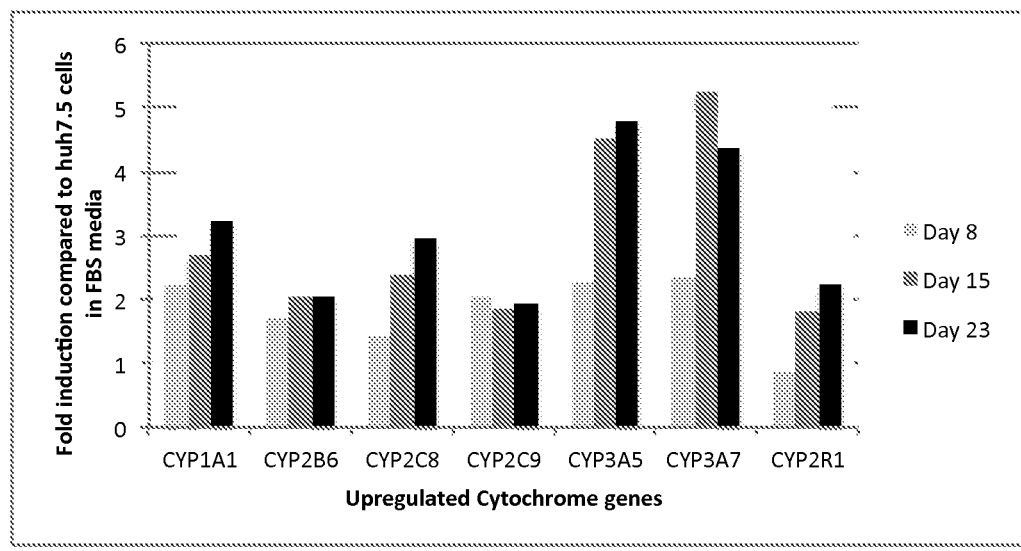
FIGS. 19 and 20 show gene expression analysis of Phase I metabolism genes in HS-cultured Huh7.5 cells.
Figure 20:
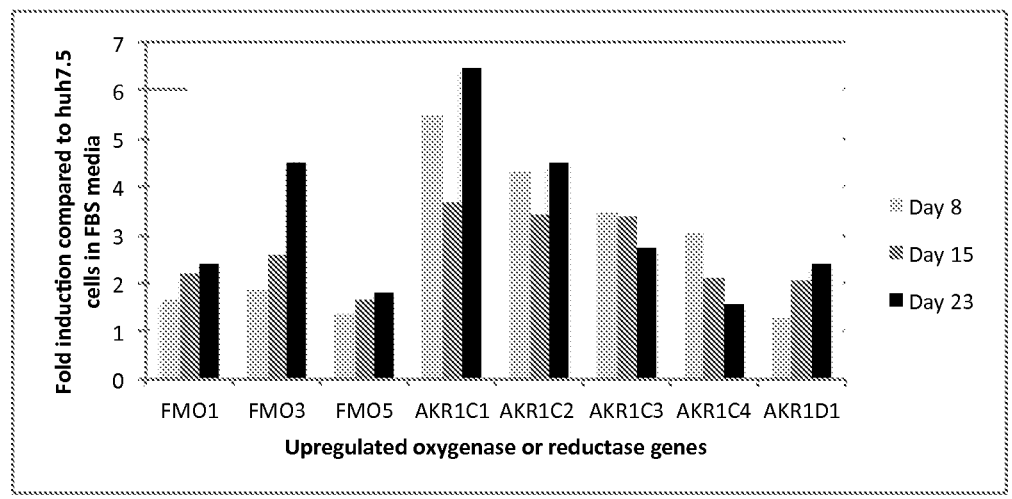
Figure 21:
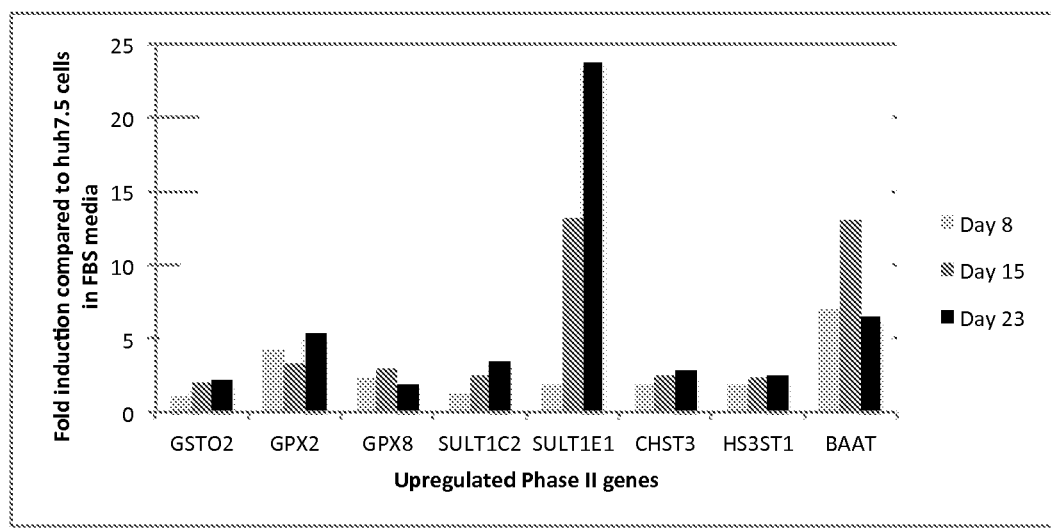
FIGS. 21 and 22 show gene expression analysis of Phase II metabolism genes in HS-cultured Huh7.5 cells.
Figure 22:
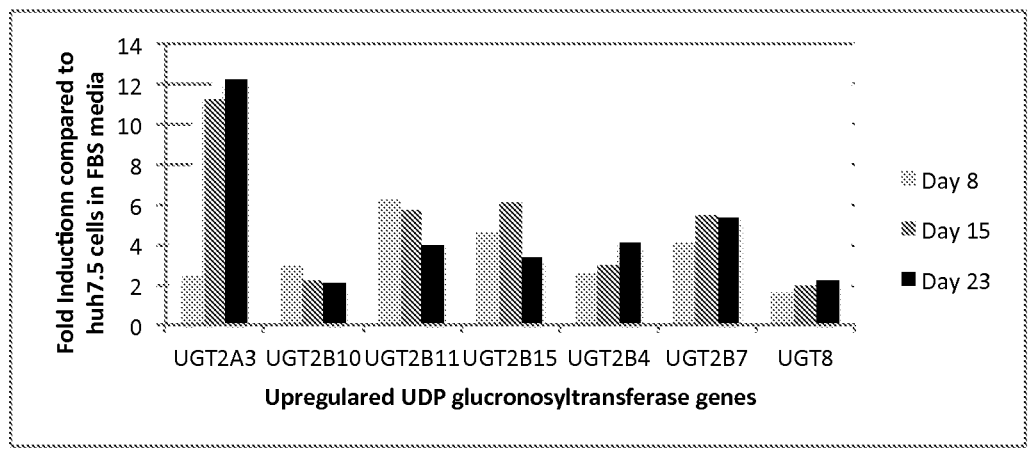

Strikingly, a number of Phase I genes were upregulated including a number of cytochromes and flavine monooxygenases and aldo-keto reductases (FIGS. 19-20). In addition glucuronosyltransferases and some other Phase II genes were upregulated (FIGS. 20-21). Many of the other genes in the various families were not upregulated, which is expected since no drugs were added to the cells.

SULTE1, an estrogen preferring sulfotransferase involved in drug metabolism was upregulated 23 fold, and a Phase II enzyme BAAT, a bile acid acyl transferase, was upregulated 13 fold. Many of the mRNAs that are upregulated in these studies seem to encode enzymes involved in bile acid metabolism, which is consistent both with differentiated liver cells and with increased detoxification function, This indicates that HS cultured cells better reflect primary hepatocytes. Such differentiated cells can provide a more consistent model than primary hepatocytes, since primary hepatocytes are normally isolated from sub-standard tissue (since the best livers are in general destined for transplantation).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of producing a cell culture comprising cells having a primary human hepatocyte phenotype, the method comprising:
   culturing a human hepatocellular carcinoma (hHCC) cell line in a culture medium comprising human serum for more than 11 days,
   wherein said culturing is without subculturing after 10 days of culturing in the culture medium comprising human serum,
   wherein said culturing does not comprise transforming the hHCC cell line, and
   wherein said culturing induces differentiation of the hHCC cell line into a cell having a primary human hepatocyte phenotype.

2. The method of claim 1, wherein the culture medium comprises about 1% to 20% human serum.

3. The method of claim 1, wherein the culture medium comprises about 2% to 10% human serum.

4. The method of claim 1, wherein the hHCC cell line is a HuH-7 or HuH-7-derived cell line.

5. The method of claim 1, wherein the culturing comprises culturing the hHCC cell line in the culture medium comprising human serum for more than 14 days.

6. The method of claim 1, wherein the culturing comprises culturing the hHCC cell line in the culture medium comprising human serum for more than 21 days.

7. The method of claim 1, further comprising assessing an effect of a candidate agent on the cell having a phenotype of a human primary hepatocyte, the method comprising:
   contacting the cell having a primary human hepatocyte phenotype with a candidate agent; and
   assaying for the presence or absence of an effect of the candidate agent on a phenotype of the cell having a phenotype of a human primary hepatocyte.

8. The method of claim 7, wherein said assaying is for an effect of the candidate agent on lipid metabolism by the cell having a phenotype of a primary human hepatocyte.

9. The method of claim 7, wherein said assaying is for an effect of the candidate agent on very low density lipoprotein (VLDL), low density lipoprotein (LDL), and/or high density lipoprotein (HDL) secretion by the cell having a phenotype of a primary human hepatocyte.

10. The method of claim 1, further comprising assessing metabolism of an agent by the cell having a phenotype of a human primary hepatocyte, the method comprising:
    contacting the cell having a primary human hepatocyte phenotype with an agent; and
    assaying for the presence of absence of a metabolite of the agent and/or the agent.

11. The method of claim 10, wherein the agent is a drug.

12. The method of claim 1, further comprising assessing toxicity of an agent on the cell having a phenotype of a human primary hepatocyte, the method comprising:
    contacting the cell having a primary human hepatocyte phenotype with an agent; and
    assaying for the presence or absence of a change in a phenotype of the cell which is indicative of toxicity of the agent for the cell.

13. The method of claim 12, wherein the phenotype is an increase in transaminase in culture medium.

14. The method of claim 12, wherein the phenotype is an increase in a marker of cell death.

15. A method of producing viral particles, the method comprising:
    incubating a cell culture comprising a human hepatocellular carcinoma (hHCC) cell line in a culture medium comprising human serum for more than 11 days,
    wherein said incubating is without subculturing after 10 days of culturing in the culture medium comprising human serum,
    wherein said incubating does not comprise transforming the hHCC cell line, wherein said incubating induces differentiation of the hHCC cell line into a cell having a primary human hepatocyte phenotype;

introducing a genome of a hepatotrophic virus into the cell having primary human hepatocyte phenotype; and maintaining the cell culture under conditions suitable for production of viral particles.

16. The method of claim 15, wherein said introducing is by adding infectious viral particles to the culture medium.

17. The method of claim 15, wherein said introducing is by infection of the hepatotrophic virus and the cell culture comprises lipoprotein-depleted serum.

18. The method of claim 15, wherein the method comprises isolating viral particles from the culture medium.

19. A method for screening a candidate agent for antiviral activity, the method comprising:

incubating a cell culture comprising a human hepatocellular carcinoma (hHCC) cell line in a culture medium comprising human serum for more than 11 days, wherein said incubating is without subculturing after 10 days of culturing in the culture medium comprising human serum wherein said incubating does not comprise transforming the hHCC cell line, wherein said incubating induces differentiation of the hHCC cell line into a cell having a primary human hepatocyte phenotype;

introducing a genome of a hepatotrophic virus into the cell having primary human hepatocyte phenotype;

contacting the cell culture with a candidate antiviral agent;

maintaining the cell culture under conditions suitable for viral replication; and detecting the presence or absence of an effect of the candidate agent upon viral replication;

wherein a decrease in viral particle production in the presence of the candidate agent as compared to the absence of the candidate agent indicates the candidate agent have antiviral activity.

20. The method of claim 19, wherein said introducing is by adding infectious viral particles to the culture medium.

21. A method for screening a sample suspected of containing an antibody for antiviral activity, the method comprising:

incubating a cell culture comprising a human hepatocellular carcinoma (hHCC) cell line in a culture medium comprising human serum for more than 11 days, wherein said incubating is without subculturing after 10 days of culturing in the culture medium comprising human serum wherein said incubating does not comprise transforming the hHCC cell line, wherein said incubating induces differentiation of the hHCC cell line into a cell having a primary human hepatocyte phenotype;

introducing a genome of a hepatotrophic virus into the cell having primary human hepatocyte phenotype;

contacting the cell culture with a sample of suspected of containing an antibody;

maintaining the cell culture under conditions suitable for viral replication; and detecting the presence or absence of an effect of the sample upon viral replication;

wherein a decrease in viral particle production in the presence of the sample as compared to the absence of the sample indicates the sample contains an antibody having antiviral activity.

22. The method of claim 21, wherein said introducing is by adding infectious viral particles to the culture medium.

23. The method of claim 1, further comprising screening for a candidate agent for the treatment of a lipoprotein mediated disease, the method comprising:

contacting a cell culture comprising the cell having a primary human hepatocyte phenotype with the candidate agent; and assaying the cell culture for the presence or absence of an effect of the candidate agent on the levels of lipoprotein secreted by the cell having a primary human hepatocyte phenotype as compared to a control sample;

wherein an effect of the candidate agent on the levels of lipoprotein secreted by the cell having a primary human hepatocyte phenotype indicates that the candidate agent can be used for the treatment of the lipoprotein mediated disease.

24. The method of claim 23, wherein the cell culture is assayed for the presence or absence of an effect of the candidate agent on the levels of very low density lipoprotein (VLDL), low density lipoprotein (LDL), and/or high density lipoprotein (HDL) in the culture medium as compared to a control sample.

25. The method of claim 23, wherein the method is for the screening for a candidate agent for the treatment of atherosclerosis, and wherein a decrease in VLDL or LDL or an increase in HDL indicates that the candidate agent can be used for the treatment of atherosclerosis.

* * * * *